United States Patent [19]
Lowe et al.

[11] Patent Number: 5,989,923
[45] Date of Patent: *Nov. 23, 1999

[54] HOLOGRAM CONTAINING SENSOR

[75] Inventors: Christopher Robin Lowe, Saffron Walden; Roger Bradley Millington, Huntington; Jeffrey Blyth, Brighton; Andrew Geoffrey Mayes, St Neots, all of United Kingdom

[73] Assignee: BTG International Limited, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/718,311
[22] PCT Filed: Mar. 27, 1995
[86] PCT No.: PCT/GB95/00668
 § 371 Date: Oct. 28, 1996
 § 102(e) Date: Oct. 28, 1996
[87] PCT Pub. No.: WO95/26499
 PCT Pub. Date: Oct. 5, 1995

[30] Foreign Application Priority Data

Mar. 28, 1994 [GB] United Kingdom .................. 9406142

[51] Int. Cl.$^6$ ....................... G01N 33/543; G01N 33/552
[52] U.S. Cl. ................................. 436/518; 359/1; 359/3; 359/10; 359/30; 359/31; 359/32; 359/33; 359/34; 422/55; 422/57; 422/82.05; 435/7.4; 435/287.1; 435/287.2; 435/288.7; 435/808; 436/164; 436/165; 436/527; 436/805
[58] Field of Search ...................... 359/1, 3, 10, 30–34; 422/55, 57, 82.05; 435/7.4, 287.1, 287.2, 288.7, 808; 436/518, 527, 164, 165, 805

[56] References Cited

U.S. PATENT DOCUMENTS 4,986,619 1/1991 Walter et al. .
5,352,582 10/1994 Lichtenwalter et al. ................ 436/518

FOREIGN PATENT DOCUMENTS 0 255 302 2/1988 European Pat. Off. .
WO 88/07203 9/1988 WIPO .

OTHER PUBLICATIONS

R.C. Spooncer et al. "A humidity sensor using wavelength–dependent holographic . . . " Intl Jour of Optoelectrics, 1992, vol. 7 No. 3, pp. 449–452.
O. Bryngdahl. "Holography with Evanescent Waves" Jour of the Optical Society of America, vol. 59, No. 12, Dec. 1969, pp. 1645–1650.
A. Othonos et al. "Fiber Bragg grating laser sensor" Optical Engineering/Nov. 1993/ vol. 32 No. 11, pp. 2841–2845.

(List continued on next page.)

Primary Examiner—Christopher L. Chin
Attorney, Agent, or Firm—Nixon & Vanderhye

[57] ABSTRACT

The invention relates to a sensor (9) comprising a hologram (17) supported on or within a holographic support medium (10).

A species to be detected is reactive with a substance disposed throughout, the sensor (9). Optionally, a chemical reactive with a species to be detected or a specific binding conjugate of a species to be detected is disposed throughout part of or all of the sensor (9).

The resulting reaction(s) cause(s) variation(s) in the hologram (17) or holographic support medium (10) which in turn varies one or more optical characteristic(s) of the hologram (17).

The variation in the optical characteristic(s) of the hologram (17) and/or the holographic support medium (10), preferably give(s) rise to a wavelength shift in incident radiation. The variation of the optical parameter is related to the species to be detected.

The advantages of the sensor are that it is cheap, easy to manufacture and, once calibrated, reliable and robust.

23 Claims, 18 Drawing Sheets

OTHER PUBLICATIONS

J.Glanz. "Diffraction Physics redefines biosensors"R&D Biosciences & Pharmaceuticals, Mar. 1993, p. 51.

P.K. Sphon et al. "Interaction of aqueous solutions . . . " Sensors and Actuators, 15 (1988), pp. 309–324.

P.S. Vukuic et al. "Surface plasmon resonance on gratings . . . " Sensors and Actuators B. 3 (1992), pp. 155–160.

D.R. Wuest et al. "Color control in reflection . . . " Applied Optics, Jun. 10, 1991, vol. 30 No. 17, pp. 2363–2367.

BRAGG EQUATION  $\lambda pk = 2.D\,n.\cos(\theta f - \theta B)$

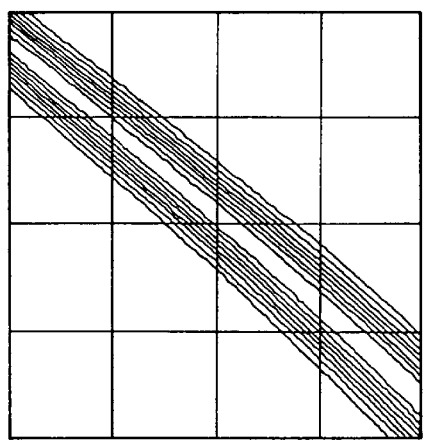
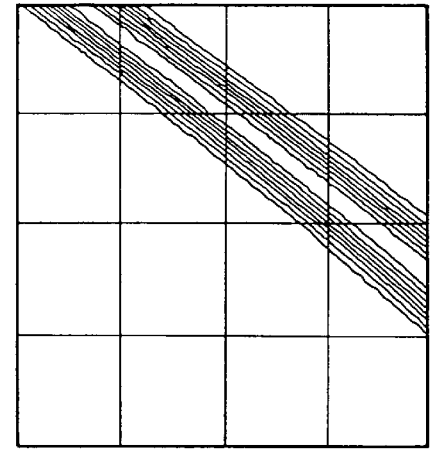
Fig. 3a                    Fig. 3b
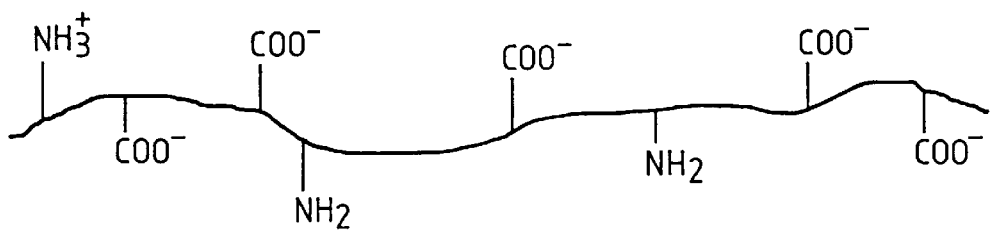
Fig. 4a
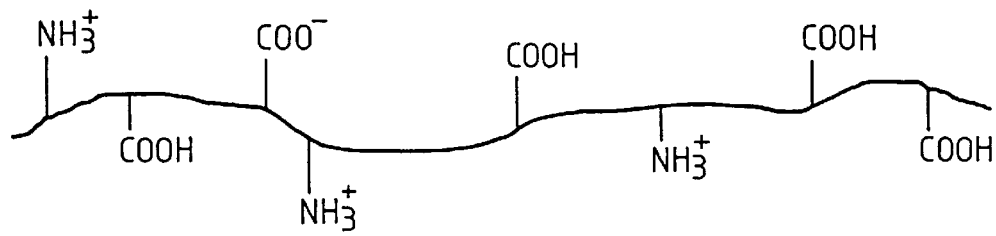
Fig 4b

| amine groups
|| carboxyl groups

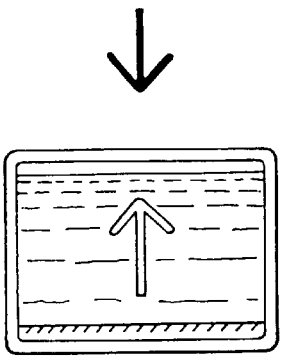
Fig. 14
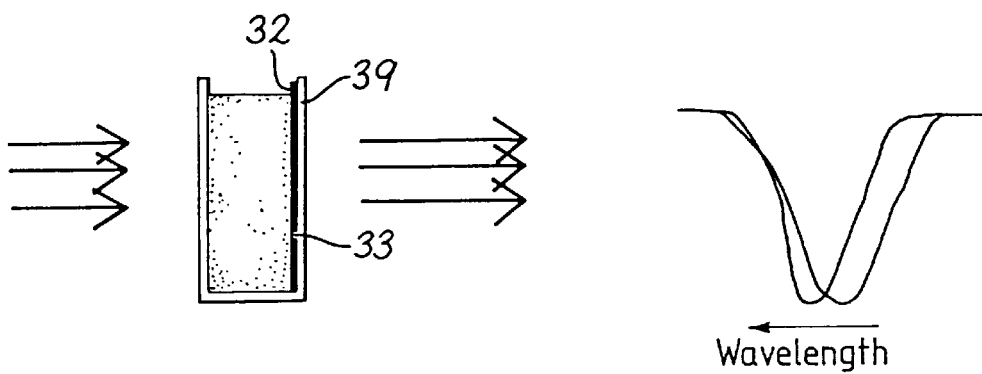
Fig. 15a
Wavelength
Fig. 15b
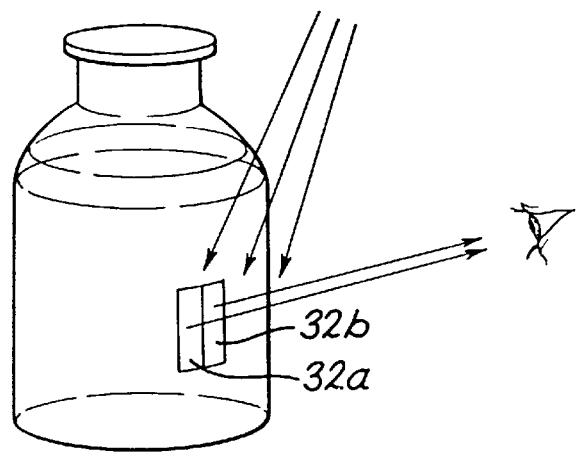
Fig. 16

HOLOGRAM CONTAINING SENSOR

This application is a 371 of PCT/GB95/00688 filed Mar. 27, 1995.

This invention relates to a sensor. More particularly the invention relates to a sensor comprising an element which affects non-ionising radiation.

Sensors which are based on electrochemical and optical principles are known. They can be colourimetric, in that a chemical reaction causes a colour change which can be measured or visualised. Sensors incorporating this technique can be embodied as a simple, easy to use, consumer diagnostic device. Other optical techniques can be incorporated into sensors. These sensors can use surface plasmon resonance, phase change on total internal reflection, optical absorption, fluorescence or change of polarisation of light. These other optical techniques and electrochemical methods require instrumentation to analyse, interpret and present the data in a meaningful form.

Whilst the aforementioned colourimetric technique is simple, it is limited to only those chemical reactions which produce a colour change. In addition, the colourimetric method may not be directly applicable to specific immunological binding events where one of the species is, for example, an antibody or antigen.

European Patent Application EP-A2-0254575 (ARES SERONO RESEARCH AND DEVELOPMENT) describes a method of treating the surface of an optical structure by using an organic polymer and solvent. The solution may contain a liquid which then binds to the surface of the optical structure. The surface of the optical structure may have a diffraction grating applied to it.

International Patent Application WO-A1-8807203 (ARES SERONO RESEARCH AND DEVELOPMENT) describes a method of treating the surface of an optical structure by forming on the surface of the structure a thin layer of material, capable of cross-polymerising on exposure to light. The material may be in the form of a diffraction grating. The optical properties of the diffraction grating may be altered when complex formation occurs between a bound ligand and its specific binding partner. An optical structure incorporating this feature can form the basis of an assay method.

European Patent Application EP-A3-0112721 (COMTECH RESEARCH UNIT LIMITED) describes an assay technique in which optical properties of a surface of a structure are varied. The variation in the optical properties arises as a result of chemical binding of a species onto a thin film, which has been applied to the surface of said structure. Optical properties are compared before and after binding and/or variation of optical properties may be observed during binding.

International Patent Application WO-A1-9009576 (PLESSEY OVERSEAS LIMITED) describes a biosensor, for detection of a species. The sensor has a diffraction grating formed by a material coated on its surface. The optical properties of the diffraction grating vary upon interaction between the material forming the diffraction grating and the species to be detected.

An article entitled "Diffraction Physics Redefines Biosensors" by James Glanz of Idetek USA appeared in R & D Magazine, p.51, March 1993, describing a surface diffraction grating consisting of antibodies, formed by irradiating an original immobilised layer with a parallel striped pattern of UV light to leave unexposed stripes of active antibody.

European Patent Application EP-A3-0167335 (NICOLI AND ELINGS) describes a method of detecting a binding reaction between a ligand and anti-ligand whereby the optical properties of a grating formed from the anti-ligand surface stripes are altered by the process of binding.

A paper appearing in Sensors and Actuators, 15, 309–324, 1988 (SPOHN AND SEIFERT) describes the use of optical grating couplers as sensors whereby the optical properties of the couplers are altered by interaction of aqueous solutions with the grating via modification to refractive index in the environment of the grating structure.

All of the aforementioned documents describe devices and/or methods for detecting a species, wherein an optical property of the device or grating on the surface of the device, is varied by addition of the species (to be detected) to an optical element. The optical element is, in all the devices, a surface mounted (or supported) diffraction grating.

Several authors for example, Kersey et al., Opt. Lett., 18, 16, 1370–1372, Aug. 15, 1993 and Meltz et al., OSA Technical Digest, vol 2, part 1, 163–166, Jan. 27–29 1988, describe in-fibre Bragg grating sensors whereby strain and/ or temperature changes cause separation of Bragg planes to change and optical properties of the grating to alter. The sensitive part of these devices is a volume element which is sensitive to only temperature and pressure, there being no intended or incidental chemical interaction with the bulk medium.

Gelatin, a derivative of the protein collagen, has been used extensively in photosensitive materials since its application by Maddox in 1871. It has been known for some time that it swells as it takes up water from its environment. Fine-grain silver-halide-sensitised emulsions have been the industry standard photosensitive material for holographic recording. A short communication to the International Journal of Optoelectronics, 7, 3, 449–452, 1992 by Spooncer et al. entitled "A humidity sensor using a wavelength-dependent holographic filter with fibre-optic links", describes response of gelatin-based Bragg reflection holograms to ambient humidity. They conclude that optical response to an increasing and decreasing cycle of humidity shows a hysteresis which limits its industrial application as a humidity sensor. The holographic element is made from commercially-available unmodified gelatin holographic AGFA (Registered Trade Mark) film.

An object of the present invention is to provide a sensor for use as a bio-sensor which, amongst other things, is easily and cheaply manufactured; requires little or no complex optical or electronic processing; may be readily modified to detect a variety of species; and is robust.

According to the present invention there is provided a sensor comprising: a holographic element, which comprises a support medium supporting a hologram, wherein at least one optical characteristic of said holographic element varies as a result of a variation of a physical property occurring throughout the bulk of the holographic support medium characterised in that said variation in a physical property arises as a result of a biochemical reaction between the support medium and a species to be detected.

The biochemical reaction may involve a chemical reaction with a known compound or element. A suitable species is advantageously disposed on the surface of, or throughout the volume of, the sensor.

The physical property of the holographic element which varies may be its volume, shape, density, viscosity, strength, hardness, charge hydrophobicity, solvent swellability, integrity or any other physical property. Variation(s) of the, or each, physical property, in turn, cause(s) a variation of an optical characteristic, such as polarisability, reflectance, refractance or absorbance of the holographic element.

The hologram may be disposed on or in, part of or throughout the bulk of the volume of the support medium. An illuminating source of non-ionising radiation, for example visible light, may be used to observe variation(s) in the, or each, optical characteristic of the holographic element.

The physical property of the support medium which varies is preferably its volume. Alternatively the property which varies is the ability of the support medium to support a regularly-spaced distribution of complex index of refraction The first of the aforementioned properties may be varied upon absorption of, or removal of, a liquid, such as water. The second property may be varied by chemical or biochemical action on the support medium.

Preferably the sensor includes a holographic element comprising a medium containing a spatial distribution of modulated complex index of refraction, which can be modified by the addition of an analyte species, such that the spectral and/or directional nature of incident radiation is modified in dependence upon a variation in said spatial distribution of modulated complex index of refraction.

Preferably the sensor comprises at least one species adapted to vary the distribution of modulated complex index of refraction upon interaction of the analyte species with a compound or element. The term modulated complex index of refraction is described below. Interaction may be chemical or physical. If the interaction is chemical it may be advantageous to have a specific binding conjugate of the analyte species disposed throughout at least part of, or all of, the support medium, or another component of the sensor.

Non-ionising radiation may be affected in one or more different ways. Preferably non-ionising radiation experiences a phase shift as a result of modification to the distribution of complex index of refraction arising from a change in spacing between peaks of a distribution supported in part, or throughout the volume of, the support medium.

More than one hologram may be supported on, or in, a sensor. Means may be provided to detect the, or each, variation in radiation emanating from, and having interacted with, the or each hologram, arising as a result of a variation in the, or each, optical characteristic. The holographic elements may be dimensioned and arranged so as to sense two independent events/species and affect simultaneously, or otherwise, radiation in two different ways.

Different types of hologram exist. One or more of these may be produced in, or on, the holographic support medium. Some different types of hologram are described below.

The term modulated complex index of refraction in general in a holographic element can refer to the modulation of the complex argument in the mathematical expression describing the electric field for non-ionising radiation. Light may be considered in terms of one or more electric fields. It is convenient, for holographic purposes, to envisage the electric field of light in a medium as comprising two components: one real (R); the other imaginary (I). This system of nomenclature is standard in holography and is used within the present specification to describe the effect a holographic element has on incident, non-ionising radiation. For example, when a hologram causes interference, by division of wave fronts in a form of diffraction grating.

A holographic element with the properties of an AMPLITUDE hologram comprises a 3-D distribution (modulation) of a radiation-absorbing material wherein the distribution is a physical record of an original interference pattern. Peaks of the modulation are referred to as fringes. Absorption of a propagating E-field in space can be introduced mathematically into the argument of the wave function by the imaginary component (I) of the refractive index. This describes how field amplitude is reduced along the direction of propagation.

A holographic element with the properties of a PHASE hologram may comprise a 3-D distribution (modulation) of refractive index where the distribution is a physical record of the original interference pattern. The peaks of the modulation are referred to as fringes. The phase of a propagating E-field in space can be represented mathematically in the argument of the wave function by the real (R) component of refractive index.

A hologram can have the properties of a PHASE or an AMPLITUDE hologram or both simultaneously.

Holograms can be further categorised into four distinct types which can co-exist in the same support medium. These are transmission, reflection, edge-lit and surface.

A TRANSMISSION hologram is one where the emergent rays leave the holographic support medium via the surface opposite to that by which incident rays enter. Fringes are usually inclined to the surface at a considerable angle, e.g. typically around 90 degrees.

A REFLECTION hologram is one where rays leave by the same surface at which incident rays enter. Fringes are usually substantially parallel to the surface of the holographic support medium (e.g. around 0 degrees).

EDGE-LIT holograms are ones where rays leave the hologram substrate or bulk of holographic support medium (e.g. glass plate) via a surface which is substantially 90 degrees to that via which incident rays enter. Fringes are usually angled with respect to the surface, typically around 45 degrees.

Of the aforementioned holograms, usually reflection or edge-lit holograms are of a so called THICK volume type if there are many fringes (i.e. modulation cycles) counted within the volume of the holographic support medium in a direction perpendicular to the surface of the holographic support medium. The fringe planes, which may be flat or curved, are termed Bragg planes. The theory of Bragg reflection is predominant.

THIN type holograms also exist, when there are relatively few fringes. A hologram can be in an intermediate volume regime between THIN and THICK. The extent of the regime increases with modulation depth.

A SURFACE hologram is one where the surface of a medium is contoured with an appropriate spatial amplitude and with a regularly spaced pattern so that it is capable of diffracting and/or reflecting light. This has the properties of another type of PHASE hologram by virtue of creating a path difference between diffracted and/or reflected rays arriving at a common point from each point on its surface. If such a surface is defined on a transparent medium then light transmitted through the medium is subjected to periodic phase changes across the surface due to the variation in optical path length imposed by the refractive index of the bulk of the medium.

The relationship between some important parameters and measurands in TABLE 1 below, have been investigated with regard to holographic structures. For example, Kogelnik (H. Kogelnik, "Coupled Wave Theory for Thick Hologram Gratings", Bell System Technical Journal, 48, 9, 2909–2947, Nov. 1969) used coupled wave theory to describe Bragg diffraction in THICK optical holograms. Thus by judicious choice of dimensions, type(s) of hologram and which internal parameter(s) is/are to be varied, different measurands may be observed. TABLE I is given to assist the skilled person to select which parameter may be varied. It is not intended to provide an exhaustive list of parameters, nor are the following equations the only equations inter-relating the parameters.

TABLE 1

| Internal Parameters | Symbol | Measurands | Symbol |
|---|---|---|---|
| Refractive index | n | Peak wavelength diffracted | $\lambda_{pk}$ |
| Refractive index modulation | $n_o$ | Bandwidth | $\Delta\lambda$ |
| Fringe spacing | D | Diffraction efficiency | $\eta$ |
| Fringe angle | $\theta_f$ | Incident angle | $\theta$ |
| Grain size | $\phi g$ | Modulation transfer function | MTF |
| Absorption modulation | $\alpha_o$ | Bragg angle of incidence | $\theta_B$ |
| Medium thickness | t | | |

Equations 1 to 4 below relate some of the various parameters and measurands in TABLE 1. Visual or instrumental means may be provided to sample one or more of these automatically or manually. One or more look-up table(s) and/or processing means may be incorporated electronically into a system arranged to detect a particular species Thus for example, the Bragg condition for optimum diffraction efficiency links incident angle ($\theta$), fringe angle ($\theta_f$), optical spacing of the fringes (D) and peak response wavelength ($\lambda_{pk}$) and is expressed in Eqn. 1 as:

$$\cos(\theta_B - \theta_f) = \lambda_{pk}/2.n.D \qquad \text{Eqn. 1}$$

Incremental changes between parameters can be easily calculated by differentiation.

The diffraction efficiency describes optical properties of, the or each, hologram when replayed by incident light, generally of a broad band spectral nature. For example, in a transparent THICK reflection hologram where fringes are tilted, the diffraction efficiency is described by Eqn. 2 below $$\eta = 1/(1+(1-(\xi/\nu)^2))/(\text{sech}(\nu^2-\xi^2)^{0.5})^2 \qquad \text{Eqn. 2}$$

where $$\nu = j.\pi.n_o.t(\lambda.(\cos(\theta).(\cos(\theta)-\lambda.\cos(\theta_f)/n.D))^{0.5}) \qquad \text{Eqn. 3}$$

and where $$\xi = -\Omega t/(2.(\cos(\theta)-\lambda.\cos(\theta_f))/n.D) \qquad \text{Eqn. 4}$$

The dephasing measure denoted by $\Omega$ quantifies deviation from the Bragg condition.

The Modulation Transfer Function (MTF) depends on grain size of the holographic support medium and any modifications made to the spatial detail in the material which forms the hologram.

Bandwidth ($\Delta\lambda$) at a diffraction angle ($\theta$) is due to spacing distribution of fringes throughout the support medium. However, in reality the detected bandwidth is, in addition, a function of a finite range of viewing angles (field of view).

There are at least four basic ways to change a hologram and thereby vary an optical characteristic. A combination of one or more of these may be employed to affect a change in the hologram and/or holographic support medium, so as to give rise to a change in a physical property of the holographic element.

The first technique involves destruction of the structure of the holographic element i.e. spoiling the integrity of the holographic element. Thus the regularity of the structure of the hologram throughout the support medium and modulation depth of the fringes defining the hologram, may be destroyed and the support medium containing fringes may be progressively removed from the holographic element. For example, this can be achieved by enzyme or chemical action which cleaves bonds at specific sites in the gel which forms a structural support matrix of the holographic support medium.

FIG. 6 shows, diagrammatically, how the aforementioned phenomenon is realised in principle. For example, trypsin has been shown to act on a gelatin-based hologram so that diffraction efficiency has been changed. FIGS. 8 and 9b show graphs of the results of such an experiment. As is apparent from FIGS. 7, 8 and 9, a hologram of this type may be used as a sensor for enzymes, in that a variation in reflection or transmission of light by a hologram can be used to detect concentration of the protease. A degree of specificity in net optical response (net optical response is the combined optical output of two or more holographic elements) may be provided, for example, by application of an appropriate inhibitor to a control sample and no inhibitor to the sample used in, or on, the holographic support medium and/or hologram. Specificity to an enzyme may also be provided by including the enzyme substrate in the holographic support medium.

The second technique is to change the size of the holographic element in order to change one or more optical properties.

This may be achieved by changing for example, the active water content of the support medium. The holographic support medium preferably comprises a gel. The second technique results in two distinct applications. These are:

2a. Detection of trace levels of water in solvent using a dry support medium or, optionally, gel-based hologram. Trace active water enters the support medium, causing it to expand thereby altering an optical property.

2b. Detection of trace levels of solvent in water using a previously saturated hologram. The solvent reduces the activity of the water so that the volume of the holographic support medium reduces.

Applications 2a and 2b are illustrated by graphs in FIGS. 10 and 12 respectively. FIGS. 10 and 12 show results of a typical experiment. The details of the experiment are described below.

2c. A further mechanism is to change osmotic forces by, for example, altering the pH, i.e. pH sensitivity. FIG. 13 shows a graph of the result of a further experiment illustrating this while the holographic support medium is saturated with water.

2d. A further mechanism can be one or more in combination of: (a) addition/removal of molecules and bonds; (b) changes in local charge distribution in molecular groups; and (c) conformational changes of molecular structure. When at least one of these occur a change occurs in visco-elastic forces which hold the matrix of the holographic support medium together/apart. When, for example, water is drawn into a dry support matrix, the support matrix (the gel, for example) swells until all forces equilibrate. At this point swelling stops. A strengthening of the visco-elastic forces expels water and the shrinking support matrix causes the separation (D) and angle ($\theta_f$) of fringes to decrease. This is shown diagrammatically in FIG. 2b. A weakening of the matrix permits uptake of water and increased fringe separation.

For example, trypsin has been shown to have another effect whereby alteration of charge distribution weakens the support matrix and, subsequently whereby cleavage of peptide bonds in gel strands also weakens the support matrix allowing a saturated gel to swell, increasing fringe separation and therefore the Bragg wavelength of the hologram. FIGS. 7 and 9a show the results of such an experiment. This type of sensor may be used as an immuno-sensor. FIG. 5b shows diagrammatically how this phenomenon may be realised in principle.

The mechanism for modification of the sensor, for example, for use as an immunosensor is such as to ensure the holographic support medium (or holographic element as a whole) is prepared so as to contain a first molecular species which is the specific binding conjugate of an analyte. Analyte molecules, with at least two functional groups or those attached to a label molecule with at least two functional groups, will bind specifically to at least two of the first species so as to form a cross-link between separate parts of the support matrix, thereby altering the visco-elastic properties of the support matrix. Consequently, if present within a water-containing environment, and the support matrix changes, the support matrix contracts and the separation (D) of the fringes is reduced. This change in fringe separation (D) may be measured by peak (Bragg) wavelength change at a fixed angle of incidence/diffraction or by monochromatic intensity change at a fixed angle or by an angle change at monochromatic peak intensity. Specificity in the technique (described above at sub-paragraph 2d) may be provided by ensuring that specific binding sites are provided within the gel matrix.

The third technique is to change the modulation of complex index of refraction by chemical modification of the holographic element, in order to change one or more optical properties. For example, an enzyme can initially enhance the depth of the modulation of complex index of refraction by cleaving at sites in between fringes. This phenomenon is shown for the example of trypsin by the initial gain in total net reflectivity in the low concentration trace of FIG. 8.

The fourth technique is to prepare the holographic element so that its response to an interaction with an analyte is a temperature change. One or more dimensions of the holographic element, for example, will change as a result of the temperature change. This results in a change in one or more optical properties. Temperature sensitivity of a reflection hologram is shown in FIG. 22.

If any of the four above mentioned mechanisms occur, whilst the hologram is being replayed by incident broad band, non ionising electromagnetic radiation, then an optical property varies and a colour or intensity change, for example, may be observed. Detection is by measuring any of the measurands in TABLE 1 as appropriate to the parameters changed. The nature of the relationships between some parameters and measurands are illustrated in equations 1–4.

Judicious selection of hologram type, fabrication technique and analyte species therefore permits a number of different sensors to be produced. Such sensors may be tailored to detect specific compounds, events or biological species. Their sensitivity may be varied by careful choice of specific binding conjugate, type of hologram and fabrication technique used. Thus a sensor having both quantitative and qualitative sensing properties may be made cheaply and easily.

It is understood that the above mechanisms are not an exhaustive description of the possible mechanisms. Furthermore it is understood that applications described are by way of example only and are not considered to be the only types of application. Examples of support media are described below.

The holographic support medium is one in which a hologram can be made and which is capable of exhibiting one or more of the properties of the sensitive mechanisms described above.

Preferably, the support medium comprises a native or modified matrix with visco-elastic properties which alter as a result of an interaction with an analyte species.

An example of such a material is gelatin which is a standard material used in holography for supporting photosensitive species, such as silver halide grains. Alternatively, gelatin can be photo-cross-linked by chromium III ions, between carboxyl groups on gel strands. Other examples of holographic support media are:

i) K-carageenan.

ii) agar or agarose.

iii) polyvinyl acohol (PVA).

iv) the broad classification of a sol-gel.

v) the broad classification of a hydro-gel.

vi) acrylates.

It will be appreciated that many types of holographic support media exist and the above list is not exhaustive.

Examples of analytes which may be identified and quantified by the invention are:

| | |
|---|---|
| water and specifically water activity | enzymes |
| ions | proteins |
| haptens | gases |
| oligonucleotides | metabolites |
| cells | viruses |
| aldehydes | bacteria |
| formaldehydes | fungi |
| | yeasts |

The aforementioned list of analytes is given by way of example only. Other analyte species may exist and could be identified with a suitable sensor, in accordance with the present invention.

In some cases, sensitivity and detection is facilitated by any binding system, where either partner is incorporated into the holographic support medium and the other is the analyte. Examples are:

| | |
|---|---|
| enzyme-substrate | dye-protein |
| ligand-protein | coenzyme-protein |
| carbohydrate-lectin | DNA-DNA |
| DNA-protein | hapten-antibody |
| antigen-antibody | ligand-receptor |
| catalytic systems | enzymes (catalytic antibodies) |
| imprinted polymers | |

Embodiments of the present invention are now described, by way of examples only, with general reference to the Figures and with particular reference to FIGS. 14 to 21, in which.

Figure 5A:
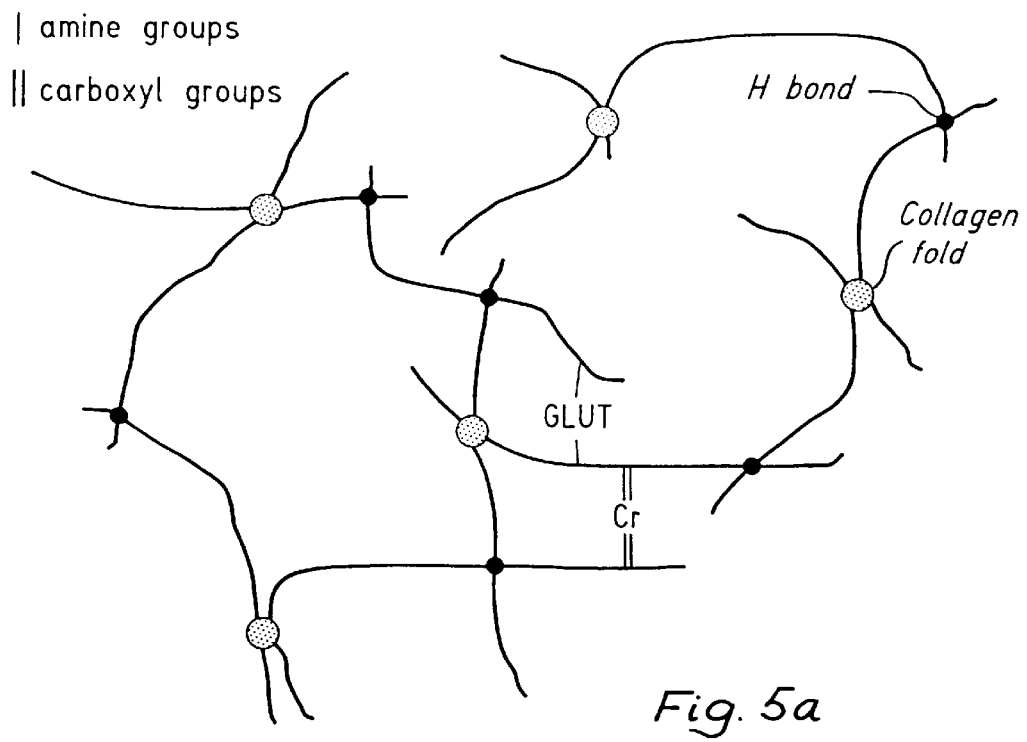
Figure 5B:
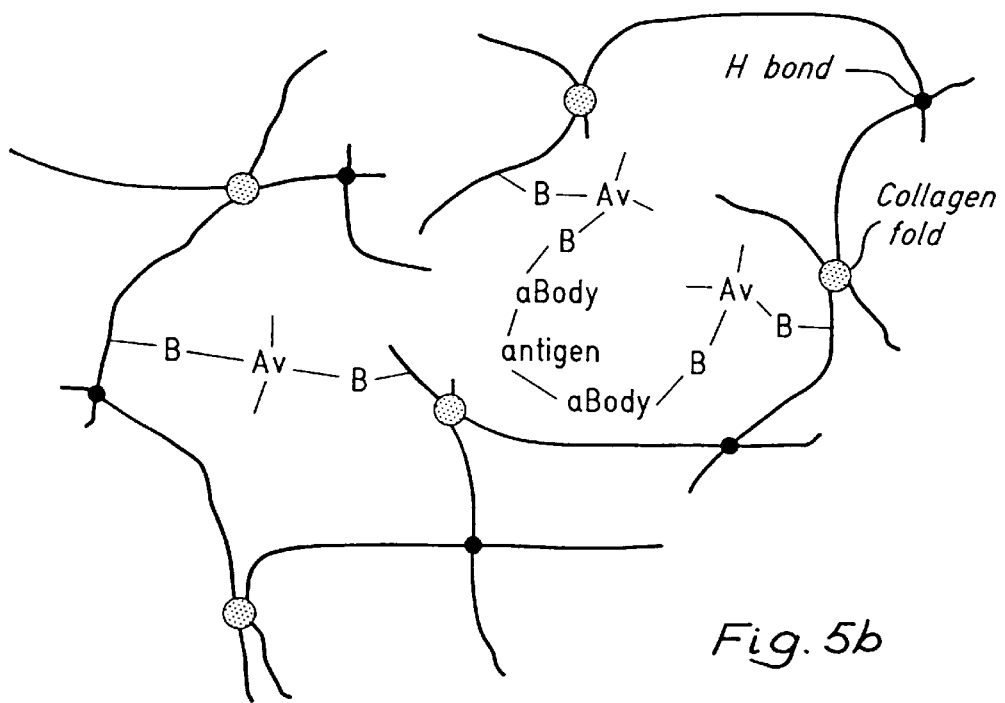
Figure 5C:
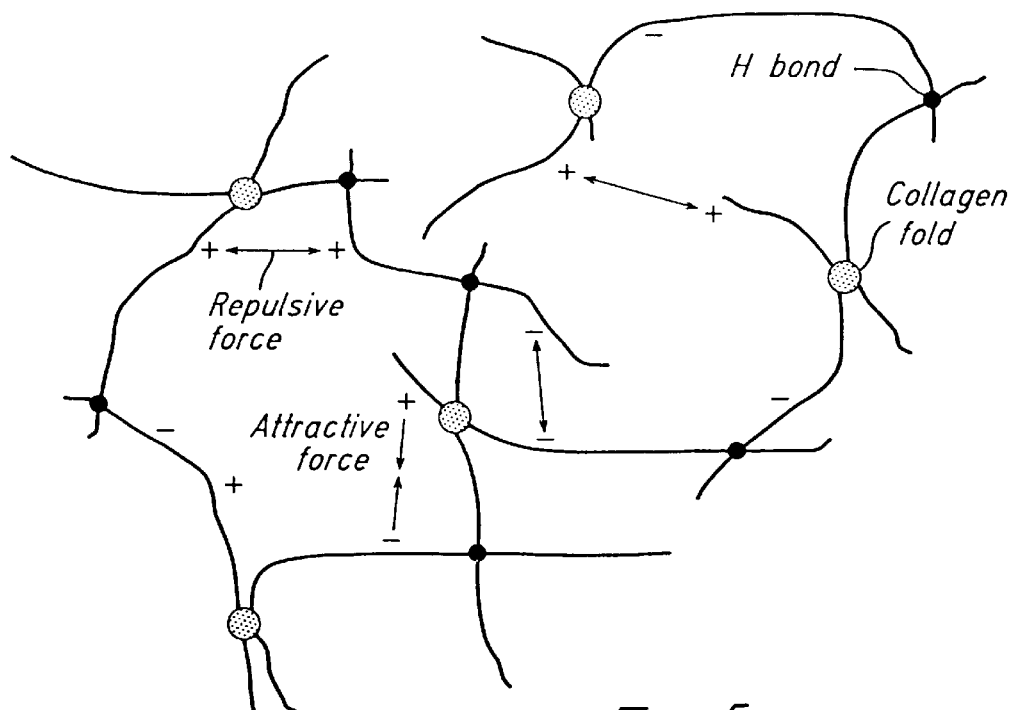
Figure 5D:
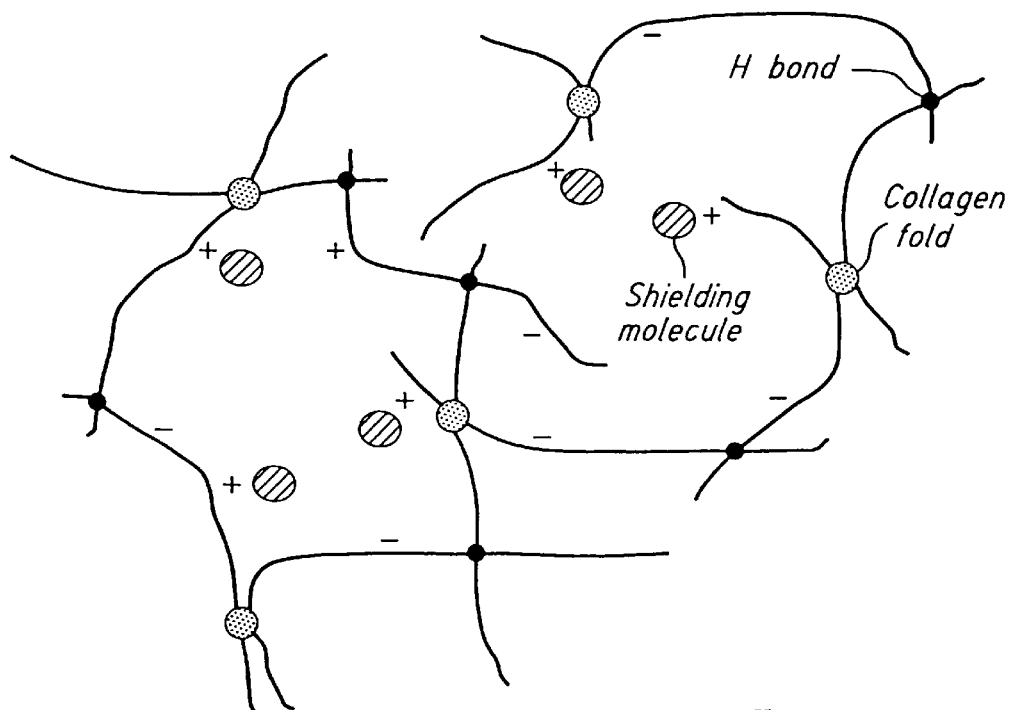
Figure 6:
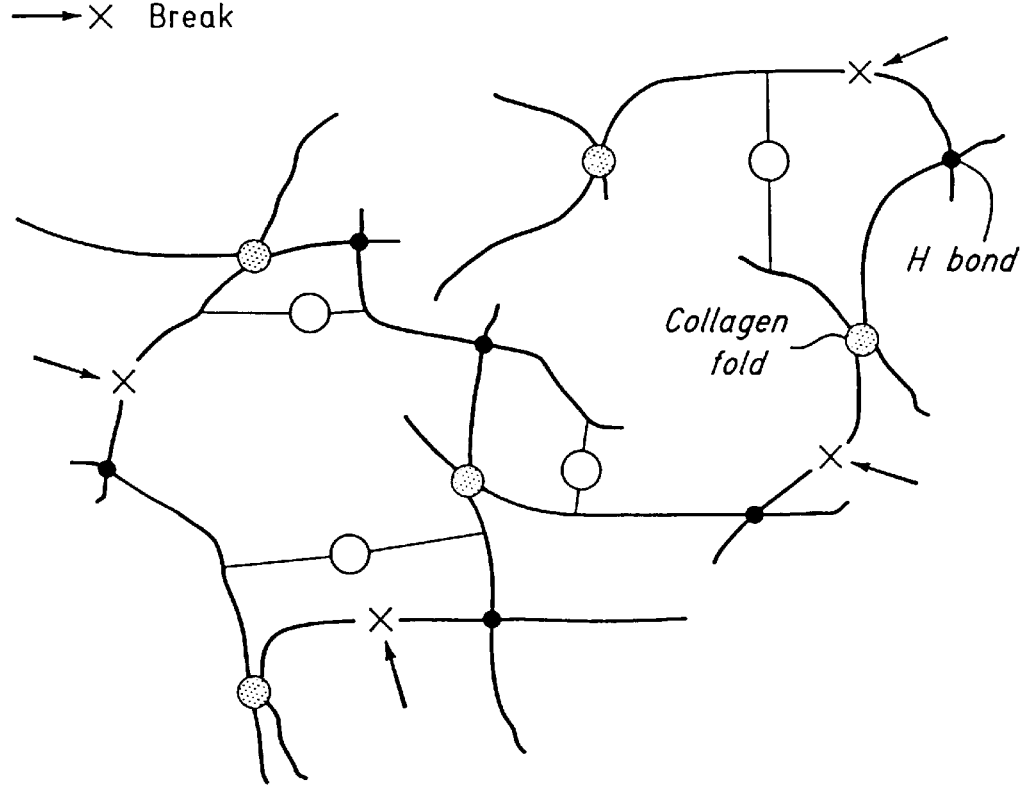
Figure 7:
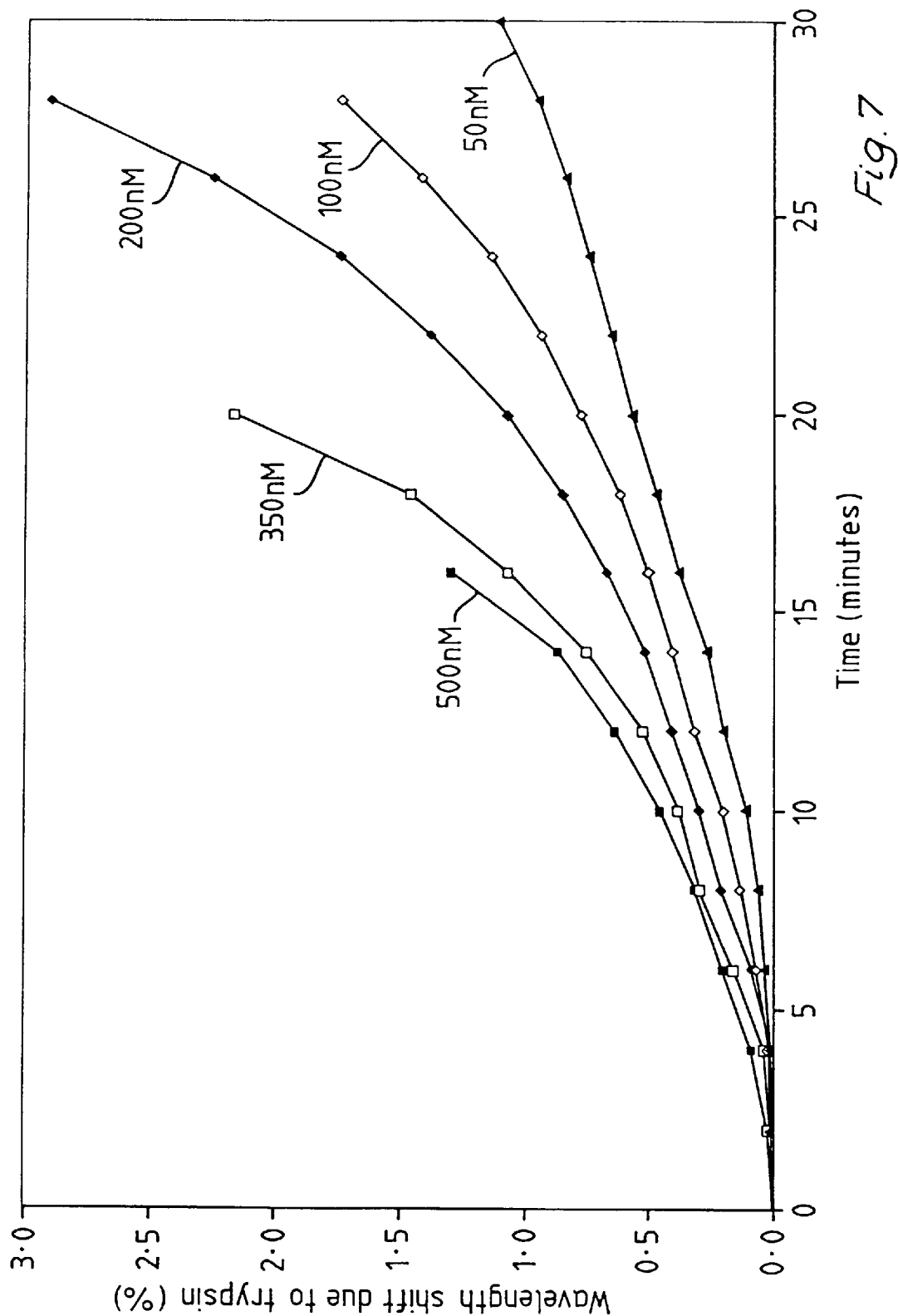
Figure 8:
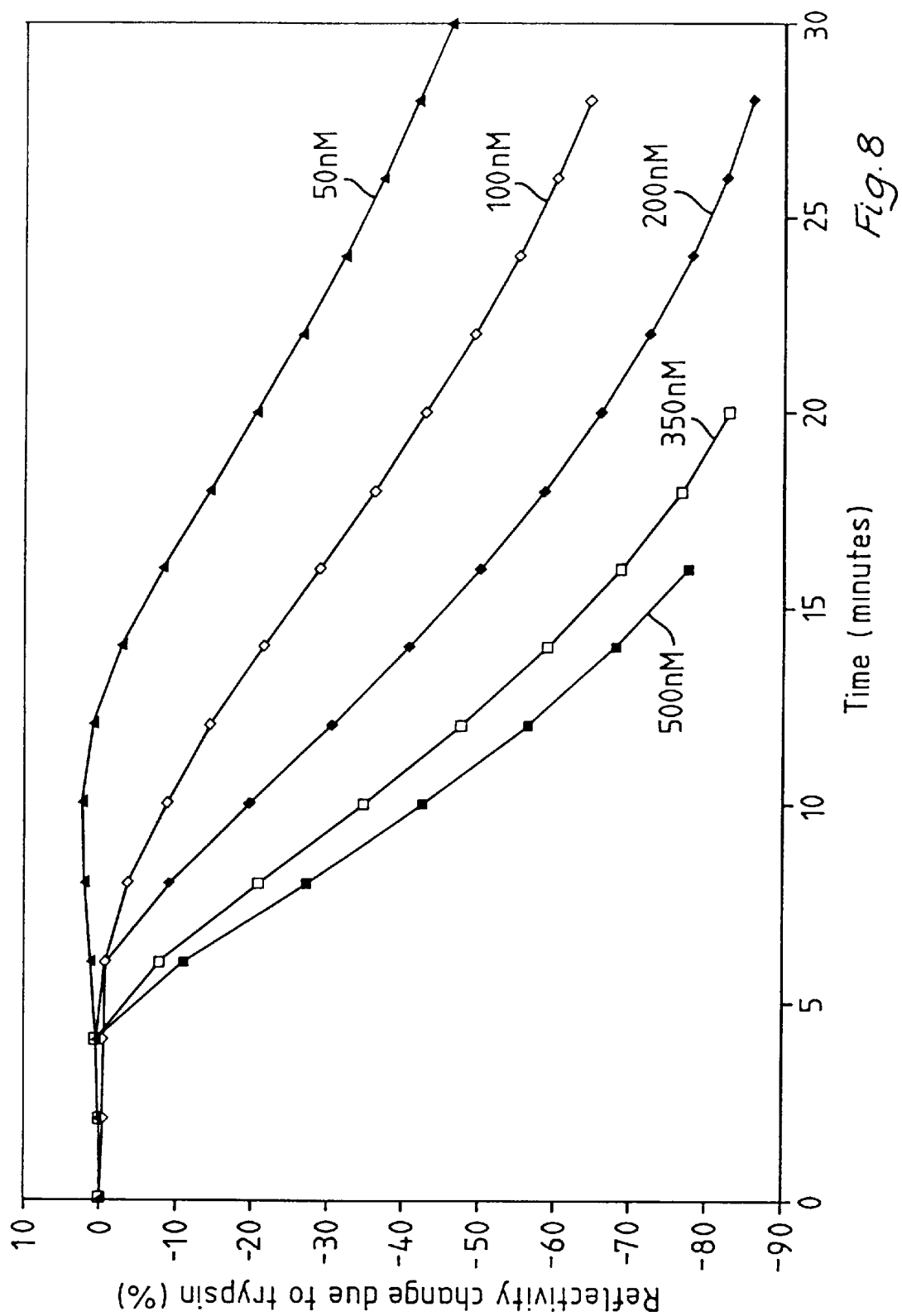
Figure 9A:
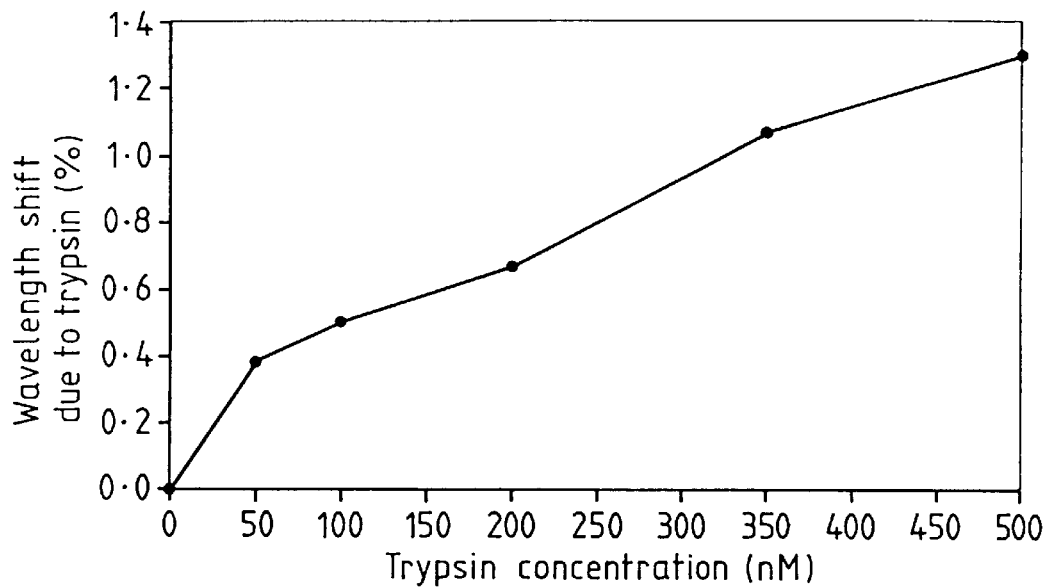
Figure 9B:
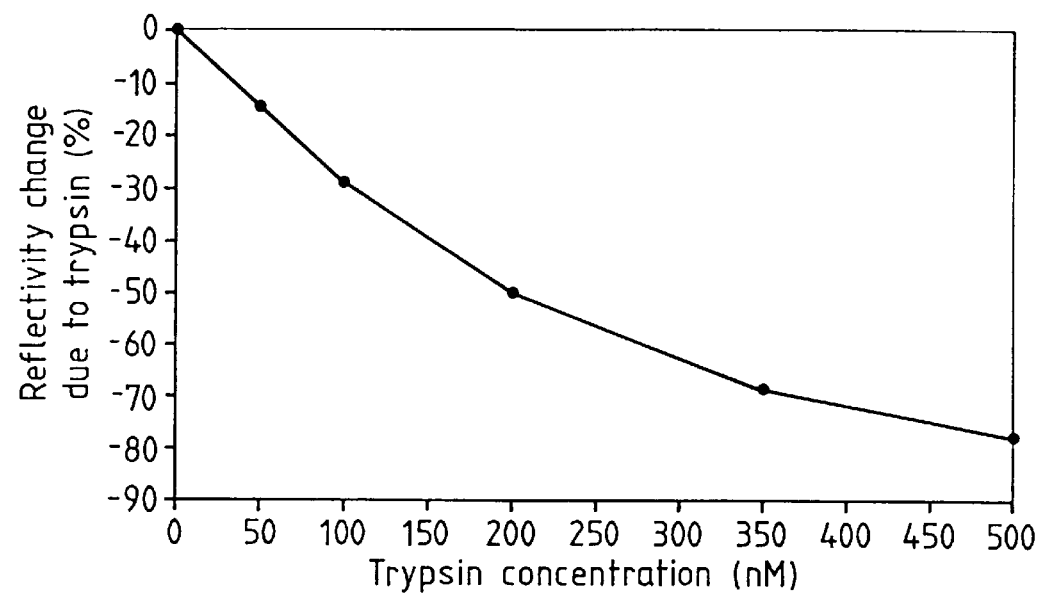
Figure 10:
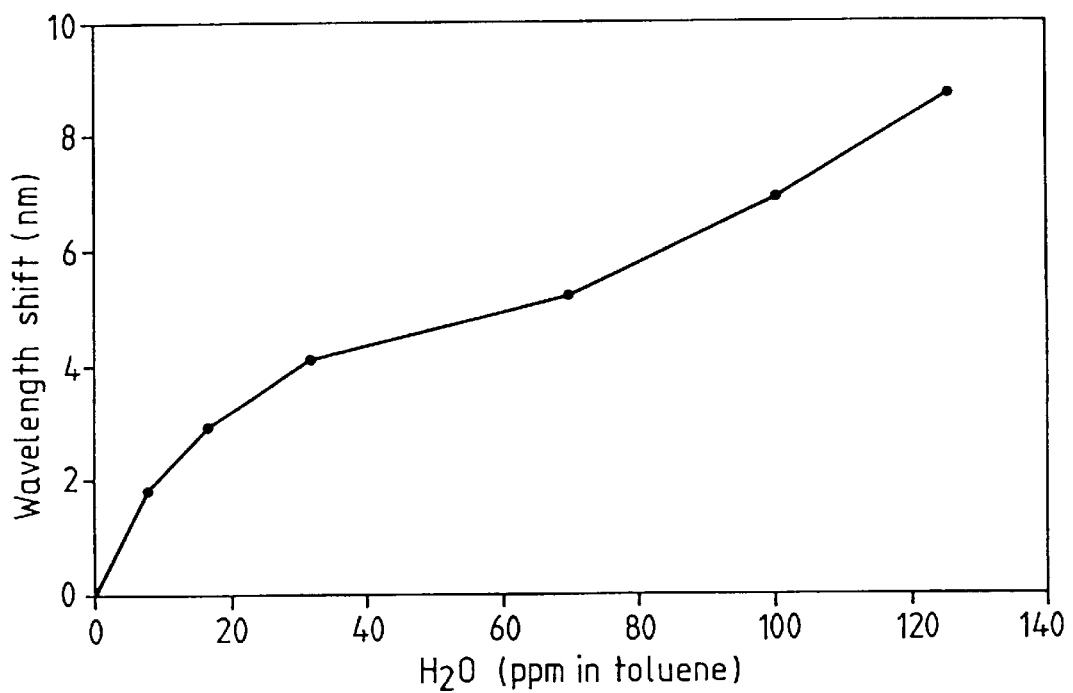
Figure 11:
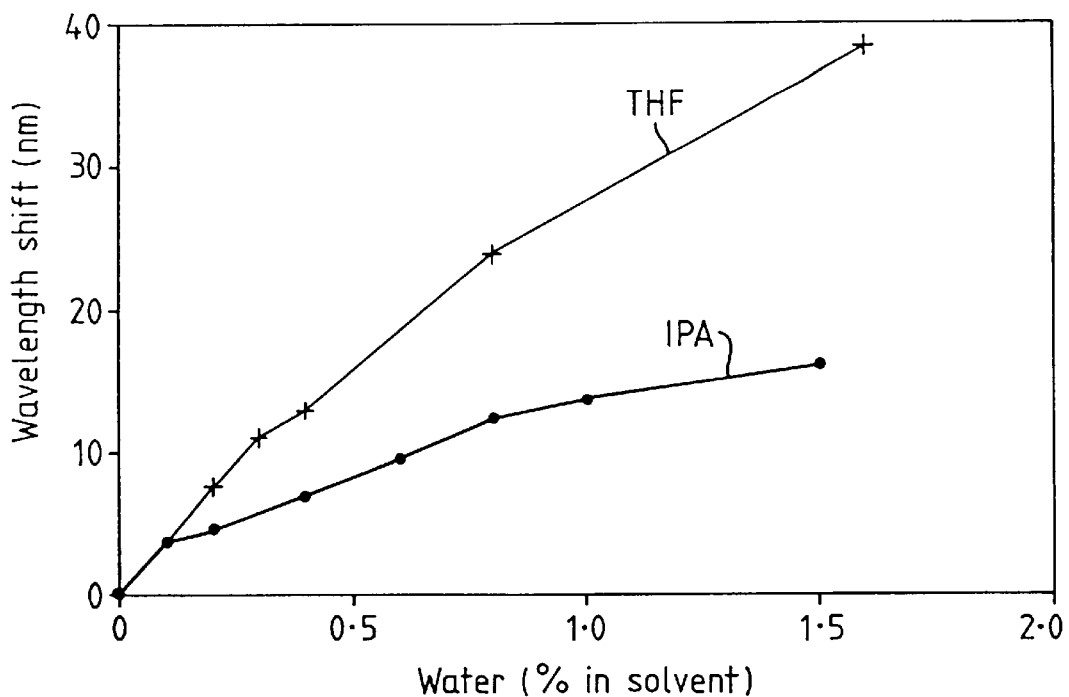
Figure 12:
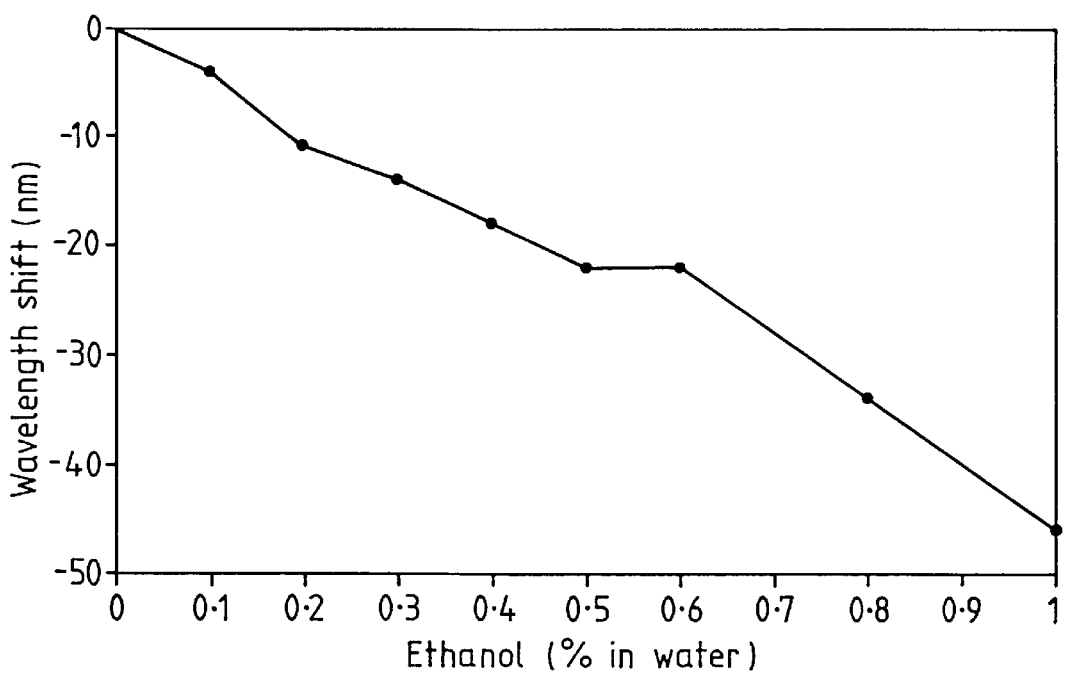
Figure 13:
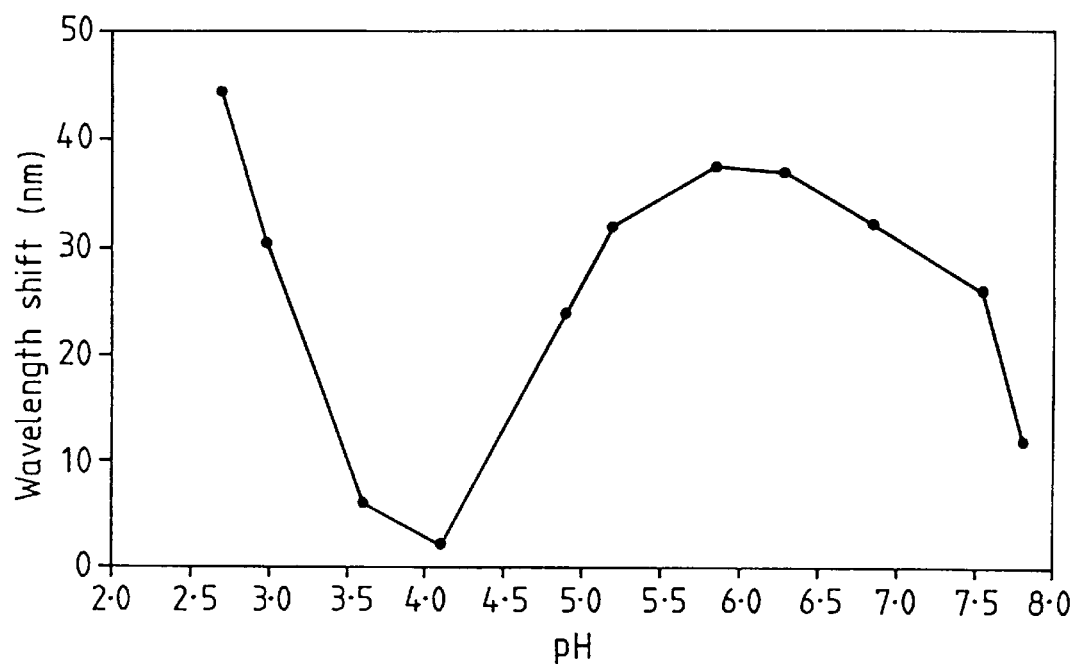
Figure 17A:
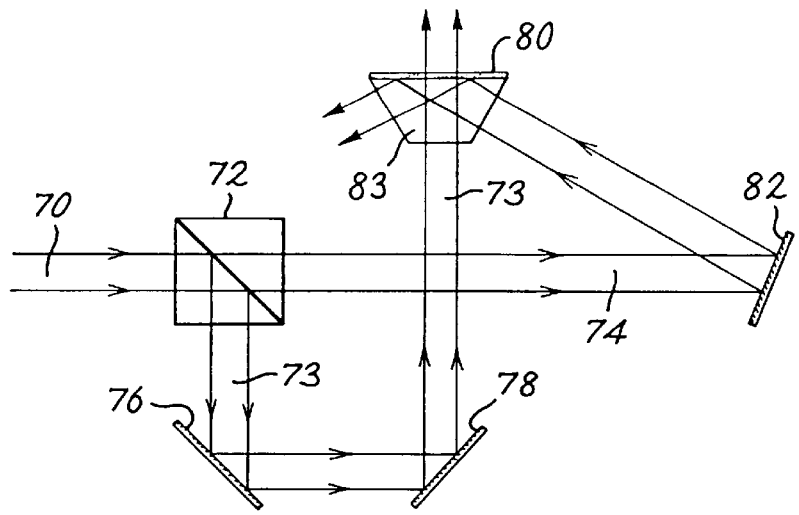
Figure 17B:
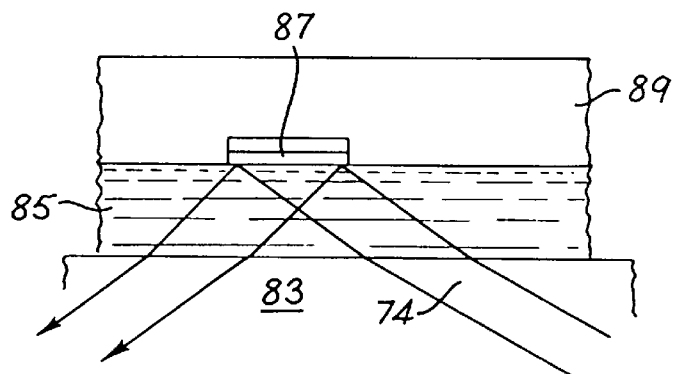
Figure 18:
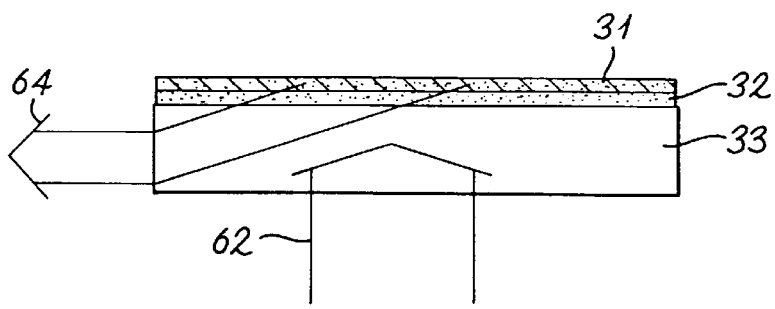
Figure 19:
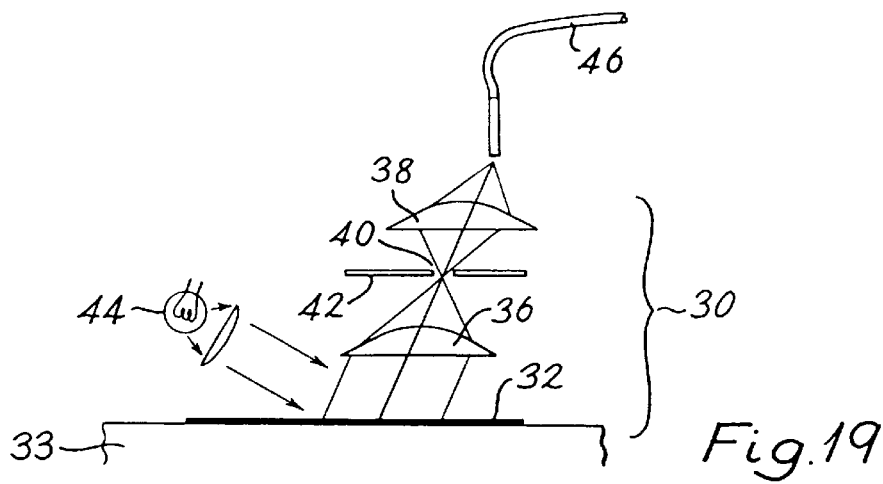
Figure 20:
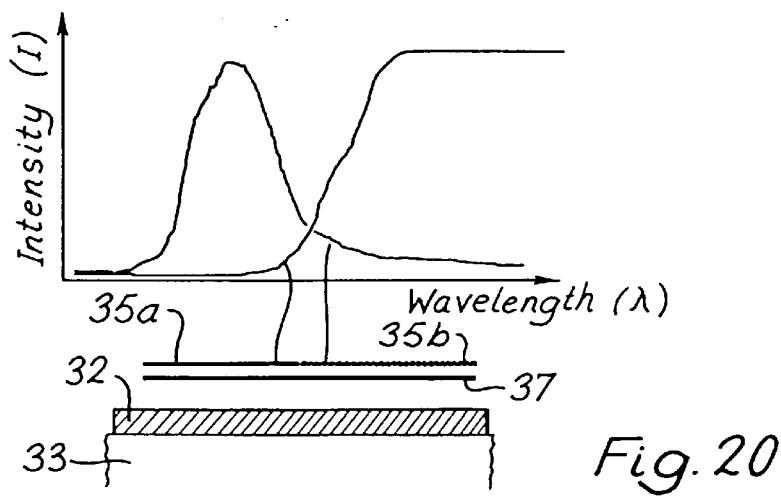
Figure 21:
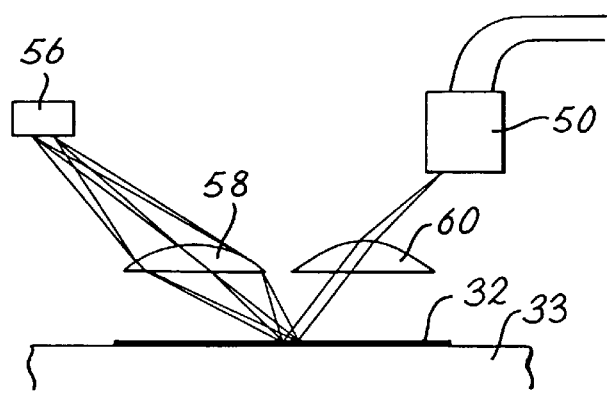
Figure 22:
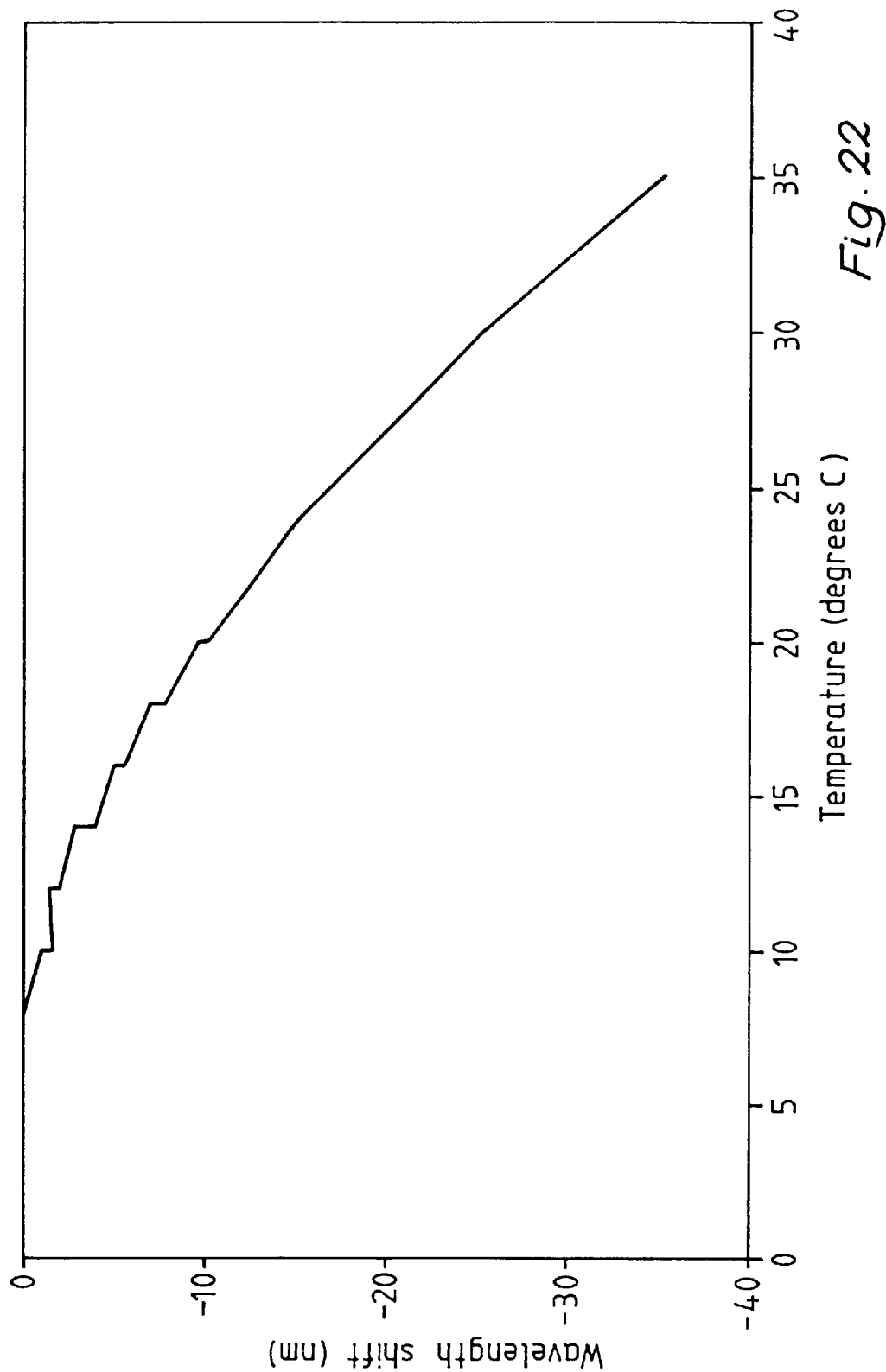
Figure 23A:
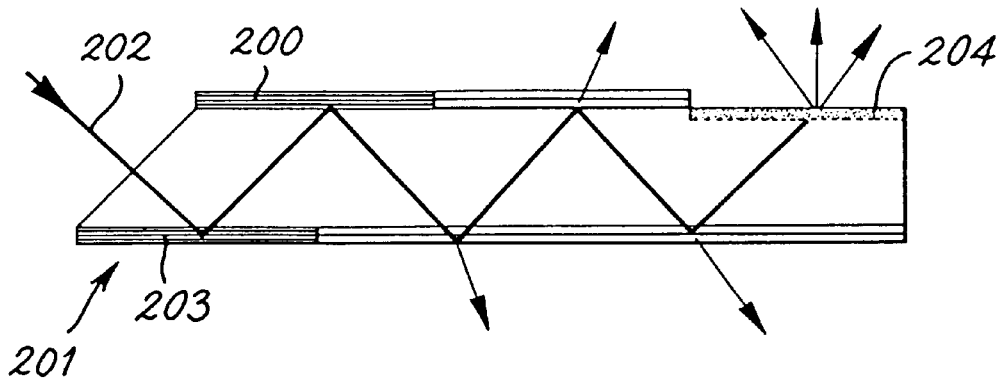
Figure 23B:
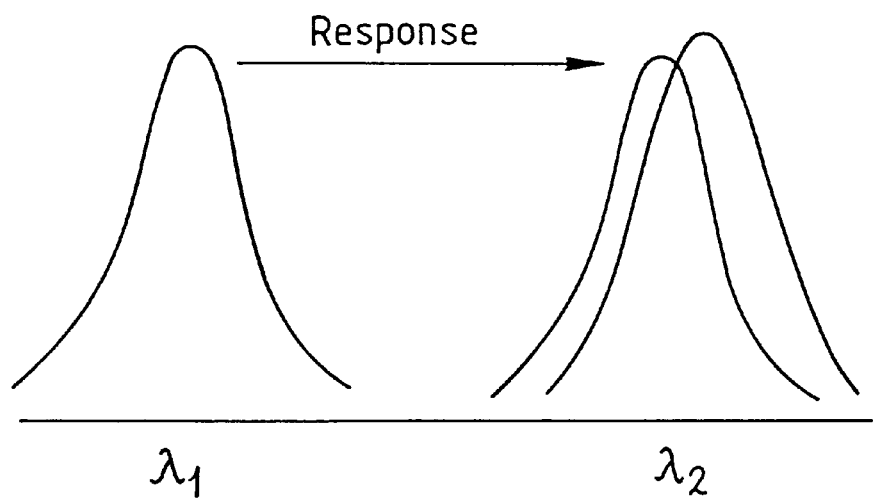
Figure 24A:
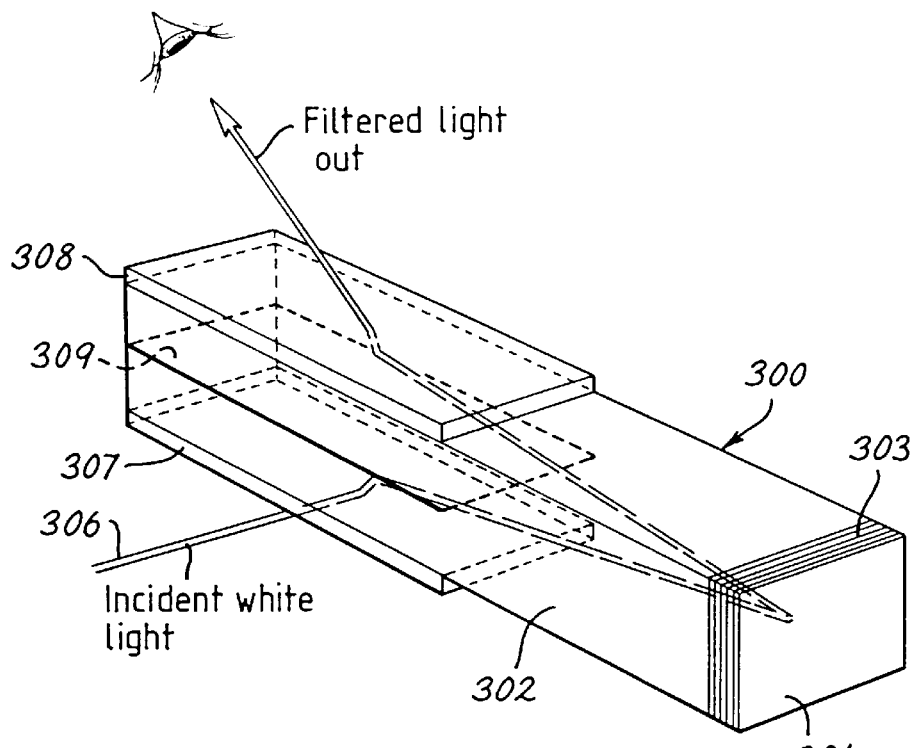
Figure 24B:
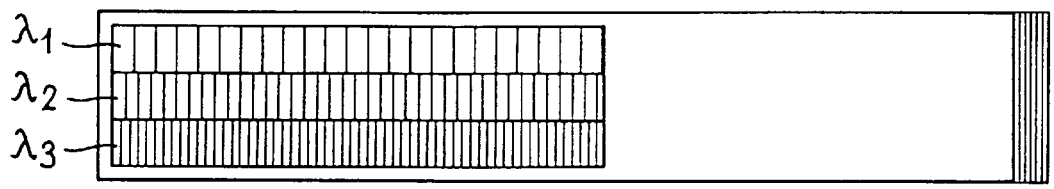

FIG. 3a, and 3b show contour plots of passband characteristic of reflected intensity, as a function of wavelength and incident angle;

FIG. 3a shows plots where there is no size change;

FIG. 3b shows a plot where the size change (wX) is 10%;

FIGS. 4a and 4b show diagrammatic sketches of gelatin strands with amino and carboxyl groups;

FIGS. 5a to d show diagrammatically bond linking between molecules;

FIG. 5a shows cross-links between gel strands to harden gel;

FIG. 5b shows cross-links between gel strands as a sensing mechanism;

FIG. 5c shows diagrammatically the interaction of charged groups contributing to the strength of the gel;

FIG. 5d shows diagrammatically the effect of charge shielding by an attached molecule;

FIG. 6 shows diagrammatically bond destruction occurring in a holographic support medium and illustrates diagrammatically the effect an enzyme has in breaking bonds in gel strands;

FIG. 7 shows a graph of trypsin action on a reflection hologram showing the rise in reflected peak wavelength, with time, as the support medium is weakened and swells;

FIG. 8 shows a graph of trypsin action on a reflection hologram showing initial enhancement of diffraction efficiency then loss of diffraction efficiency, measured in a spectrophotometer against time;

FIG. 9a shows a graph of trypsin action on a reflection hologram showing concentration of trypsin and peak wavelength change at timed intervals;

FIG. 9b shows a graph of trypsin action on a reflection hologram showing concentration of trypsin and peak reflectivity change at timed intervals;

FIG. 10 is a graph showing sensitivity of a reflection hologram to trace water in solvent, using a white light spectrometer at 0° incidence and relates wavelength shift (nm) to ppm water in toluene;

FIG. 11 is a graph showing sensitivity of a reflection hologram to trace water in solvents (IPA and THF) with different hydrophilicity;

FIG. 12 is a graph showing sensitivity of a reflection hologram to trace ethanol in water using a white light spectrometer at 0° incidence and relates wavelength shift (nm) with concentration of ethanol in water;

FIG. 13 is a graph showing the effect of pH on a reflection hologram using a white light spectrometer at 0° incidence and relates pH to wavelength (nm) shift;

FIG. 14 shows diagrammatically hologram construction in a cuvette with 0° reflection;

FIG. 15a shows diagrammatically hologram replay in the cuvette of FIG. 14;

FIG. 15b is a graph of signal absorbance when replaying the hologram of FIG. 14;

FIG. 16 shows diagrammatically test strips attached to the inside of a bottle containing a liquid reagent;

FIGS. 17a and 17b show diagrammatically thin hologram construction using an evanescent wave as one of the interfering beams;

FIG. 18 shows diagrammatically replay of an "evanescent-wave hologram" as embodied in a sensor;

FIG. 19 shows a fibre optic array acting as a hologram reader, at fixed viewing angle (but whole-spectrum illumination), for use in conjunction with a sensor;

FIG. 20 shows an example of a filtered visual display relying on a wavelength shift for use as a sensor;

FIG. 21 shows a fibre optic array hologram reader and holographic sensor, having a fixed wavelength but a varying Bragg angle;

FIG. 22 shows a graph of wavelength shift (nm) against temperature (° C.);

FIG. 23a shows a diagrammatical view of a holographic sensor with a reference, incorporated into a dipstick format;

FIG. 23b shows graphs of spectral shift of output signal from a reference hologram with respect to a sensor hologram;

FIGS. 24a and 24b show diagramatically another embodiment of a dipstick incorporating a specific holographic sensor and a spatially-varying indicator.

Figure 1A:
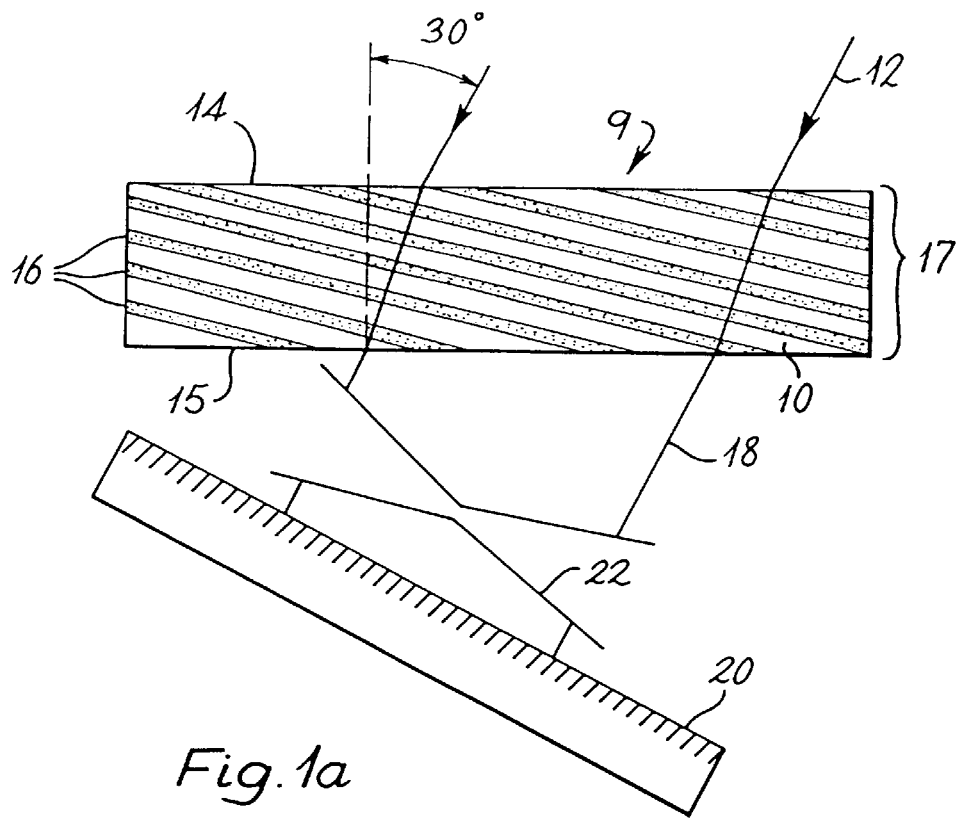
FIG. 1a shows diagrammatically one type of hologram.

Referring to FIG. 1a, a hologram element 9 comprises holographic support medium 10 and modulated complex index of refraction (fringes) 16. Fringes 16 are fabricated as follows: Incident laser light rays 12 impinge surface 14. Laser light rays 18 emerge from the holographic support medium 10 at surface 15 and are reflected off mirror 20. Interference fringes 16, defining hologram 17, are formed when reflected light rays 22 interfere with incident light rays 12. Hologram 17 is thus formed throughout the volume of the holographic support medium 10. In some variants, further chemical processing is required to complete hologram fabrication.

A detailed description of manufacture of the sensor appears below. Reference to standard techniques of emulsion preparation is made as it is considered that the skilled person is familiar with such techniques.

The principles of construction of a hologram are illustrated in FIGS. 1a, 14 and 17. Principles and examples of reconstruction (replay) of a hologram are illustrated in FIGS. 1b, 2, 15, 16 and 18.

Figure 1B:
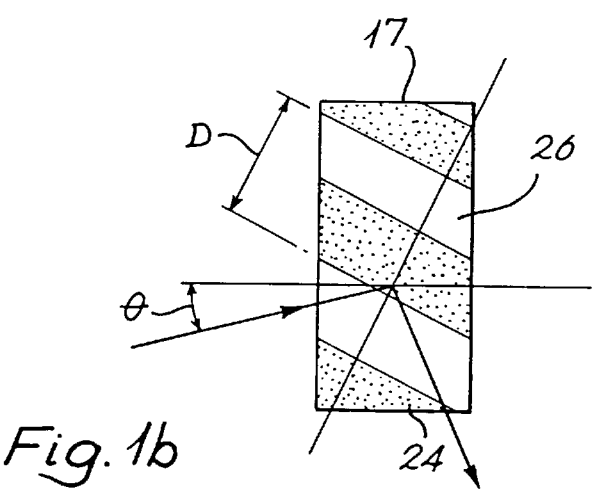
FIG. 1b shows schematic diagrams of fringes, replay rays and associated vectors.

In order to illustrate some of the sensitive detection mechanisms pertaining to the invention, brief description is made with general reference to FIG. 1b, of the diffracting and replay properties of a plane wave hologram. Specific mechanisms are described with reference to other Figures.

In general, a hologram 17 is a three-dimensional (3-D) grating which converts incident light into one or more beams having spatial and spectral dependence on the internal parameters of the hologram 17. Typically a grating comprises a refractive index or absorption modulation of the material 24 within a support matrix 26. The material 24 may be an alteration of the support matrix 26 itself. The modulation is referred to as fringes 16 as in FIG. 1a. The hologram 17 itself acts as a transducer element of a sensor if an analyte (not shown) modifies an internal parameter so as to produce a measurable change in an optical property of the hologram 17 when the hologram 17 is reconstructed or replayed.

It will be appreciated that any of the interrelated parameters and measurands shown in TABLE 1 above may be deduced from the effect.

Figure 2A:
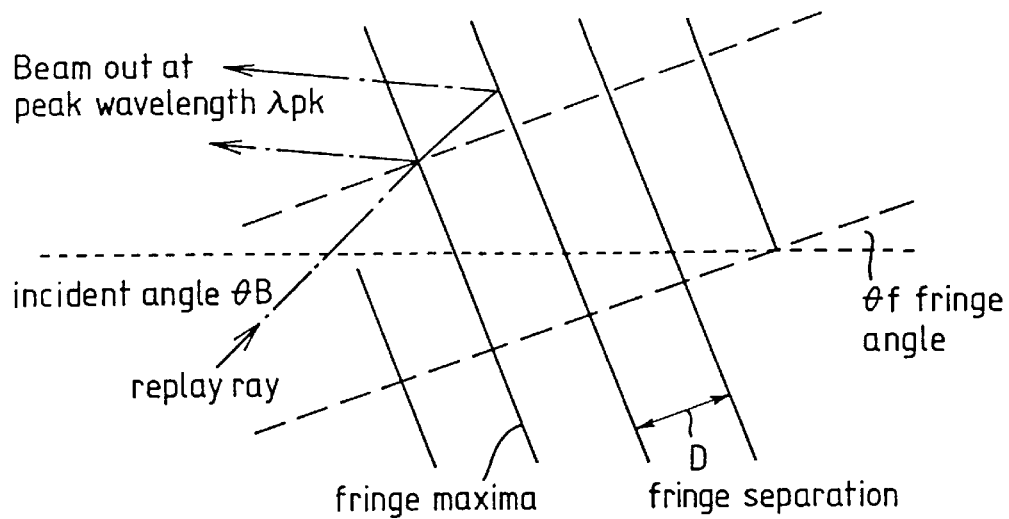
FIG. 2a shows diagrammatically some of the optical parameters referred to in TABLE 1, with reference to a ray diagram of a thick reflection hologram.
Figure 2B:
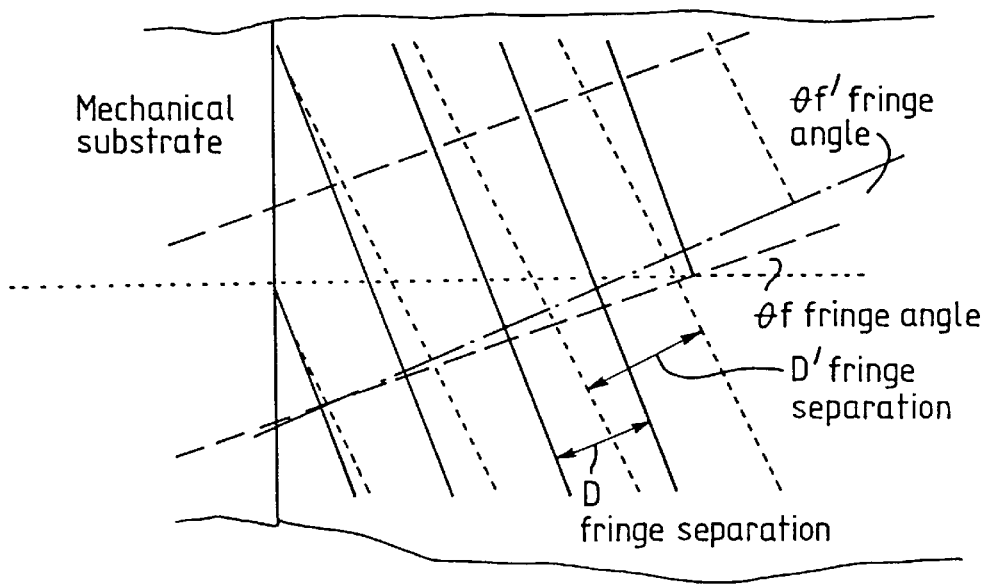
FIG. 2b shows fringe angle and separation change which occurs when there is hologram swelling.

Referring also to FIGS. 1 and 2, FIG. 6 shows, diagrammatically, the breakage of bonds (indicated with an "X") in a support matrix 26. This is believed to have two effects; weakening of the matrix 26 permits the matrix to swell (mechanism 2d above) causing fringes 16 to separate further; and Bragg wavelength or angle to increase. The regularity and integrity of the modulated complex index of refraction forming the fringes 16, is perturbed so as to reduce the optical efficiency of the hologram (mechanism 1 above). In extreme cases, material 10 containing fringes 16 is removed so as to reduce the optical efficiency of the hologram.

Referring also to FIGS. 1 and 2, FIG. 5b shows, diagrammatically, the addition of molecular cross-links in a matrix 26. Cross-linking may be provided chemically or, more specifically, by reactions between specific pairs of molecular conjugates in a binding system. This has the effect of strengthening the matrix so as to limit the extent to which the matrix can swell (mechanism 2d above). The effect is to limit the fringe separation and therefore the extent of change in Bragg wavelength or angle. If such types of cross-link are removed by whatever reaction, specific or not, then the effect is to weaken the matrix and permit it to swell. Thus the effect is to permit fringe separation and therefore Bragg wavelength to increase or Bragg angle to change accordingly.

Referring also to FIGS. 1 and 2, FIGS. 5c and 5d show, diagrammatically, the contribution of electrostatic forces to the strength of the matrix 26 whereby a shielding/revealing or other alterations of charge distribution changes the net strength of the matrix (mechanism 2d above). The effect is to change the size of the matrix, a weakening permitting swelling and a strengthening limiting swelling so that separation of fringes 16 changes accordingly and a corresponding change in Bragg wavelength or angle results. FIGS. 4 show how charges present in, for example a gelatin support matrix vary with pH. The graph of FIG. 3 shows how Bragg wavelength changes with pH (mechanisms 2c and 2d).

Other mechanisms (2a and 2b above) relate to water activity in an originally-dry and originally-saturated matrix 26 respectively. In either case water activity causes a change in the equilibrium size of the matrix 26 and FIGS. 1 and 2 illustrate how the Bragg condition is altered.

Reference is now made to particular applications of the sensor. In a particular example, the change in peak reflectivity and wavelength at fixed incident angle were measured and calibrated against trypsin concentration. Graphs of the results appear at FIGS. 9a and 9b respectively. It is readily apparent that a sensor may therefore be fabricated whose characteristics are predictable and which may be used to correlate intensity or colour of a light signal to concentration or action of proteolytic enzyme. In the example shown, the matrix which supports the hologram is gelatin, a convenient substrate for proteolytic enzymes. It is apparent that a sensor for other enzymes will be made in a support matrix containing a corresponding substrate. For example, a sensor for amylase would include a starch component in its support matrix. Furthermore, the utilisation of enzyme action can be extended to a specific system, an immunosensor, for example, where the selected enzyme is used as a label attached to an antigen bound to an antibody which is immobilised in a secondary layer above a holographic element containing the enzyme substrate. Upon exposure to antigen analyte, competitive binding releases the enzyme-labelled antigen which diffuses into the holographic element where the enzyme degrades the support matrix. Holographic optical response is a result of analyte antigen concentration and activity.

A further application is in sensing bacteria such as bacillus and pseudomonas, for example, whereby secretion of proteolytic enzymes has the above effect on a gelatin hologram, for example.

An application of a cuvette-based embodiment is for measuring water activity in solvent or reagent. For example, water in toluene has been measured down to a concentration level below the typical detection limit of an existing standard test called the Karl-Fischer method (K.F. test). The parameter changed in this case was fringe spacing and is detected as a peak intensity colour change at a fixed angle. FIG. 10 shows results obtained using the holographic sensor.

Another application of the aforementioned embodiment is measuring solvent levels in water. For example, ethanol in water was measured down to 0.1%. Again, the parameter changed is fringe spacing and is detected as a peak intensity colour change at a fixed angle. FIG. 12 shows the result obtained using the holographic sensor.

Another application of the sensor is in formaldehyde sensing, employing the aforementioned cross-linking mechanism whereby formaldehyde cross-links, for example, gelatin, pulling the gelatin molecules together thereby causing the support medium to shrink and the Bragg wavelength to reduce. This may be achieved in a matrix which has not been previously hardened via the amine groups so it is advantageous to the performance of the device to use a customised holographic support medium.

Reference is now made to particular embodiments of the sensor. It will be appreciated that these are by way of example only and variations to the embodiments described will not depart from the scope of the invention.

Embodiments of the invention incorporated into sensor systems are now described, by way of example only, and with reference to FIGS. 15, 16, 18, 19, 20 and 21, in which like parts bear the same reference numerals. The Figures show a holographic element 32 on a mechanical substrate 33. The separation or angle of the fringes (not shown) is varied, or the refractive properties of the holographic element 32 is changed causing an optical response to a variety of analytes, specifically or not, depending on their identity and on the preparative treatment given to the element 32. The identity of the analytes depends further on which of the aforementioned mechanisms are employed. The embodiments are now described.

An embodiment of the invention is incorporated into a sensor system, and is shown in FIG. 15. The sensor comprises a holographic element 32 supported on substrate 33 inside a container 39 which may be a spectroscopic or a fluorometric cuvette. The change in spectral response shown diagrammatically in FIG. 15b, to an appropriate analyte is measured via a standard spectrophotometer (not shown).

Another embodiment of the invention is incorporated into another sensor system, and is shown in FIG. 16. The sensor comprises holographic elements 32a and 32b, representing test and reference sensors respectively, where 32a and 32b are contained within a container of a liquid or gas which in turn contains an analyte. Response is visualised directly as a colour or intensity change.

Another embodiment of the invention may be incorporated into a sensor system, shown in FIG. 18. The sensor comprises a holographic element 32, comprising a hologram 31 in a support medium, illuminated by light 62 which can be of a narrow or broad-band nature. The changing intensity and/or spectral response 64 of hologram 31, to an analyte, is monitored by a photodiode (not shown) or spectral processor (not shown) or by direct visualisation.

Another embodiment of the invention may be incorporated into another sensor system, shown in FIG. 19. The sensor comprises a holographic element 32, an arrangement of lenses 36 and 38 together with a narrow aperture 40 in a suitably opaque material 42 to ensure that light from a broad-band source 44 is directed within a narrowly-defined angle of incidence to a fibre optic 46. A wavelength shift or intensity change in light reflected from 32 can be visualised as a colour or intensity change at the end of a fibre optic 46 or it can be processed by suitable electronic or spectrographic means (not shown).

Another embodiment of the invention is incorporated into a sensor system, and is described with reference to FIG. 20. The sensor comprises a holographic element 32, a message mask 37, a high-pass filter 35a and a low pass filter 35b. Passbands are also shown on the sketch of the graph of Intensity (I) against wavelength. A spectral change in the passband of the hologram in 32 as a result of an analyte interaction is visualised directly as a change from a positive to a negative indication or vice-versa.

Another embodiment of the invention is incorporated into a sensor shown in FIG. 21. The sensor system comprises an appropriate holographic element 33 supporting a hologram 32, a monochromatic light source 56, a lens 58, providing a range of angles incident onto the hologram 32, and lens 60 for focusing light onto a linear array of fibre optics 50. A change induced in the hologram 32 changes the Bragg angle which can be visualised or otherwise detected at the end of the fibre optic 50. A linear photodetector array (not shown) may be employed directly in place of the fibre array as an angle detector.

Another embodiment of the invention is incorporated into a sensor shown in FIG. 23a. The sensor comprises a first (reference) holographic element 200 supporting a hologram ($\lambda_1$), situated on a clear transparent bar or dipstick 201 shaped so that light can enter the dipstick at one end 202, thereby illuminating a test holographic element ($\lambda_2$) 203. Light is reflected at and around the Bragg wavelength within a narrowly defined range of angles so that it is incident upon the holographic element 200 which acts as a reference. The second holographic element 203 is different from the first holographic element 200 in that it will not respond to the specific analyte and in that its passband is at a longer wavelength. As long as no analyte is present then the Bragg wavelengths of the two holograms 200 and 203 do not match and light will not reach a message mask 204. When analyte is present then light is transferred along the dipstick 201 (which acts as a light pipe) and to the illuminated message mask 204 which indicates a positive response. Non-specific effects alter the two passbands equivalently. The lightpath geometry is arranged to restrict the range of angles transmitted in order to improve response discrimination. FIG. 23b illustrates diagramatically the relative spectral shift of incident light.

Another embodiment of the invention is incorporated into a sensor system 300 shown in FIGS. 24a and b. The sensor system 300 comprises an appropriate sensitive holographic element supporting a hologram 301, situated at one end of a transparent bar or dipstick 302 and at least one further holographic element 303, not sensitive to analyte. All three elements are arranged so that light path 306 is defined as shown. Side elements 307 and 308 couple light into and out of the bar respectively. More than one holographic element may be arranged in parallel adjacent strips each with a different Bragg response so that the response from each sensitive holographic element is visually apparent as a spatial change as well as a colour change. This is shown diagramatically as $\lambda_1$, $\lambda_2$ and $\lambda_3$ in FIG. 24b. An opaque screen 309 acts as a light blocker and is placed between transparent windows 307 and 308.

One particularly useful and readily achievable application of the sensor, as described in any of the aforementioned embodiments, is as a water sensor. The water sensor can be easily and conveniently manufactured. A method of manufacturing the water sensor comprising a holographic sensor is described below.

The ability to easily measure the lowest residual water content of many substances, that are generally considered to be "dry", is of great importance in many branches of industry and science. For example the water content of liquid hydrocarbons, alcohols, or ethers are routinely carried out so that chemical or biological reactions can be performed with these substances. For more than fifty years the common method used for measuring water content has been that published by Karl Fischer (KF) in 1935. This method is essentially one of titration. A non-aqueous solution of elemental iodine is added dropwise from a burette into an aliquot of substance whose water content is required to be known. The substance has to have added to it the sulphite of an amine such as pyridine whose water content has to be predetermined and allowed for. The elemental iodine and the sulphite ions attack any water molecules present to produce sulphate and iodide ions. The "end point" occurs when no more water is available and an excess of unreacted iodine appears in the aliquot.

There are a number of disadvantages in this method. Solutions require precalibration, they have a limited shelf life; and they impose handling restrictions and the need for carrying out the titrations under a fume hood.

The holographic sensor of the present invention requires only a small test strip of holographic grating to be immersed in the liquid, solid, solid-in-suspension or gas whose water content is required to be known. After a short period, typically about 10 minutes of mild agitation, to achieve homogeneity in the medium immediately surrounding the grating, the water content can be ascertained from the change in colour of the grating when it is illuminated (replayed) under a white light source. The colour change can be compared with a calibrated test chart, preferably of holographic form by the naked eye or examined using a spectroscope.

The aforementioned holographic water sensor has been found capable of measuring water content from 0.01% to 100% to within experimental error. The method of preparing the holographic grating however has to take into account whether it is to be used to measure in the lowest or highest range. The acceptable range of expansion/contraction of the grating from its original size is limited by broadening and peak reduction of the response peak as the grating "mark/space ratio" departs from unity. The mark/space ratio describes the spatial distribution of refractive index that defines the grating. Methods of construction of both gratings are described below. The method used for the lowest water levels is described first in relation to measuring trace water in solvents.

The preparation and use is now described.

A Lippmann emulsion is first coated onto a glass sheet. A typical method such as that based on the description by H. Thiry in Journal of Photographic Science, Vol. 35, 1987 may be used. The finished and dried emulsion is then exposed to monochromatic light in the simplest type of set-up to produce a holographic grating similar to that shown in FIGS. 1a and 1b. In a preferred arrangement a plane mirror reflects light through the emulsion along the normal so that it interferes with incident light to form a standing wave grating with fringes half a wavelength apart. This type of grating after processing and cutting into suitably sized strips, is intended for use in a sample cell of a spectrophotometer cuvette, for example of the type shown in FIGS. 14 and 15. A blank reference cell cuvette (not shown) consists of the same dried emulsion as in the sample cell but this strip has been exposed to white incoherent light so it does not contain a grating and by being given the same processing treatment, any intrinsic colour bias in the film is the same in the reference cell as in the sample cell as is known by a skilled person. The grating is positioned in the spectrophotometer cuvette's sample cell with its emulsion facing towards the liquid. The cuvette may need to be capped tightly to keep out atmospheric moisture. The replay wavelength is able to be monitored because the grating reflects it back along the same axis as the specularly reflected light and therefore it registers as an absorption process. As the grating absorbs moisture from the sample liquid, considerable wavelength shift can occur due to the swelling effect. The wavelength shift is dependent on the moisture uptake by the gelatin. Unlike the usual manner in which measurements are made by a spectrophotometer, the peak height is not of direct relevance.

FIG. 10 shows the sensitivity of such a sensor when used to measure water in samples of toluene that were specially prepared from extremely dry toluene, spiked with very small quantities of water. All the solutions were prepared and extracted under dry nitrogen using septum caps and syringes with fine needles. The ordinate shows absorption maxima of the spectrophotometer beam in nanometres. In the case of particularly hydrophobic substances such as toluene, the sensitivity of the sensor can be about 10 times greater than could be achieved with the Karl Fischer detection method. However, in the case of a very hydrophilic substance such as iso-propyl alcohol (IPA) the sensitivity is apparently about the same as in the Karl Fischer (KF) method.

One reason for this difference in sensitivity depending on the degree of hydrophilicity of the sample, can be explained as follows: hydrophilic groups in the polypeptide chains in the gelatin of the holographic sensor, attract water mainly through the hydrogen bonding processes. Therefore these groups have to compete with the hydrogen bonding process which gives the high affinity for water shown by, for example, iso-propyl alcohol. This results in the hologram only swelling to some equilibrium value, whereas in the case of toluene such competitive hydrogen-bonding does not occur. In the KF system the bonding energy obtained through sulphite changing to sulphate, probably means that the reaction with water is virtually fully complete in both hydrophobic and hydrophilic solvents. Therefore the KF system may be said to measure water content, whereas the holographic sensor could be said to measure water "activity". This feature gives the holographic sensor an additional advantage over the KF system when measuring water in solvents which are being used for biocatalysed reactions. In these cases it is the water activity rather than the total water content which is significant.

FIG. 11 shows results obtained with holographic sensors used to measure the water content of both IPA and THF (tetrahydrofuran). The lower hydrophilicity of THF can be seen to cause a steeper slope (higher sensitivity) than in the case of IPA. All tests were conducted at a temperature of 25° C.

The following example describes the preparation and use of a "label-based" hologram for general sensing of water in solvents.

A particularly useful feature of the sensor is that it enables very low levels of water contamination in for example, an organic solvent to be readily detectable by the naked eye and be sufficiently inexpensive to be able to be marketed, for example, as a disposable strip or label stuck to the inside of bottles of organic solvent. A technique is described below.

A grating was exposed as shown in FIG. 1 but with the monochromatic light 12 source inclined at about 30 degrees to the normal. The hologram 17 was developed and bleached in a standard manner. The purpose of making the grating off axis by about 30 degrees was to enable diffracted light not to be obscured by specularly reflected light off glass or plastic support surfaces (not shown). Two identical 1×0.5 cm strips of grating were cut out and each one was stuck to the inside wall of a 500 cc glass bottle near the base, with the emulsion side facing into the liquid. The bottles were then thoroughly dried for a half hour at 70° C. in a drying oven. Each of the two bottles were then filled with 330 cc. of anhydrous toluene and a small magnetic stirrer bar and then sealed with rubber septum caps to keep out atmospheric moisture. The bottles were positioned on a magnetic stirrer so that each one displayed an identical diffracted image of an overhead white strip light. To an observer the image of the strip light looked yellow. 50 microlitres (0.050 cc) of pure water was then injected into just one of the bottles and both bottles were stirred for about 30 minutes. When both bottles were placed side by side in a suitable viewing position of the grating, it was evident that the bottle that had been contaminated with water displayed an orange coloured grating whereas the other still displayed a yellow grating. The water content of the spiked toluene was 150 ppm. The lowest water content measurable by a typical KF system is around 1000 ppm. Therefore even without using a spectrophotometer an assessment was made by the naked eye with the holographic sensor which exceeds what is possible with a typical KF system.

The embodiment described in the aforementioned test is shown diagrammatically in FIG. 16. The holographic grating is subdivided so that a protected area of the strip can act as a control so that comparison can be made on the exposed area affected by moisture.

A sensor is fabricated for detecting water, in a gas flow. A thin strip of grating equilibrated in an ambient relative humidity of 60%, replays an orange colour under a white light source. The sensor is then placed in a transparent glass tube attached to tubing from a supply of dry nitrogen gas. A small burst of nitrogen gas causes a rapid change of colour of the grating from orange to turquoise. The effect appears almost instantaneous. Intermediate levels of humidity may be achieved by first bubbling the gas through various concentrations of sulphuric acid in a gas bubbler or Dreschel bottle. Intermediate colours between turquoise and orange can be seen in the grating and changes are so rapid that no independent means were available to verify the actual relative humidity changes in the tubing.

A hologram suitable for use at high water activity will now be described.

To use a holographic sensor in an aqueous environment as, for example, in measuring trace solvent in water, it may be necessary to make one alteration to the exposure arrangement shown in FIGS. 1a and b. The holographic support medium should be in a swollen state when the exposure to monochromatic light is made. This swelling is achieved by exposing the material while it is immersed in an aqueous solution. The reason for this is to achieve visible replay when the hologram is in the swollen state. FIG. 12 shows the effect of adding ethanol to pure water. This measures the lowering of water activity, i.e. the degree of hydrogen bonding between the gelatin of the grating and the water is reduced by competition from the hydrophilic organic solvent and hence swelling of the grating is reduced.

Trypsin Examples

A useful application of the sensor is as a sensor for the proteolytic enzyme trypsin, particularly in neonatal screening for cystic fibrosis and detection and monitoring of pancreatic disorders in general. An example of a method describing a holographic sensor for this type of application appears below.

Trypsin is produced by the pancreas and secreted into the human digestive system. Its identification is an indicator of pancreatic exocrine function. An important example of trypsin detection in medicine is in screening for cystic fibrosis during the neonatal period when elevated (by a factor of two or three) levels of blood immunoreactive trypsin or reduced levels of intestinal trypsin give a positive response to the condition. It is important to identify the disease as soon as possible in order that treatment of the secondary pathology can commence. There are a few screening methods, the most reliable and specific of which is an expensive and time consuming radioimmunoassay for blood trypsin. Only those tests which prove positive are followed-up by a relatively low cost test for elevated levels of sodium and chloride ions in sweat.

A simple test for trypsin in stool samples is based on the destructive action of the enzyme on the gelatin layer of an X-ray film. The end point is defined as the dilution of the stool at which the dissolution of the film is not visually observed. The test is not specific or quantitative.

The response of a gelatin-based reflection hologram to trypsin has been shown as a function of nominal concentration down to 50 nM in, FIG. 9. Duodenal trypsin is normally likely to be in the range 250 nM to 3000 nM. It is therefore possible to calibrate such a device to give a quantitative indication of trypsin concentration. Improvement to the device tested can be obtained by softening the gelatin to obtain greater sensitivity and by making a thinner film to obtain an even faster response.

The holographic sensor described when applied to trypsin, provides a faster. cheaper and quantitative alternative to existing tests.

In one preferred embodiment, a sample of stool or duodenal fluid is applied to the test hologram which is replayed via an optical path which is preferably situated away from the sample site. Preferably, the illuminating source is a light emitting diode and the detector is a photodiode so that a measurement of intensity is interpreted as trypsin concentration using low-cost readily available electronic processing equipment. A reference hologram, pre-treated with trypsin inhibitor, provides a correction for interfering components in the sample.

In another preferred embodiment, the test hologram is made in a support medium which consists, in total or in part, of substrate material specific to trypsin i.e. containing predominantly lysine or arginine functional groups.

A preferred hologram type is an edge-lit, thin hologram, as described previously, created using interference between one or more evanescent light beams and one or more evanescent or homogeneous beams. These terms are familiar to one skilled in the field of optics and holography. The method by which an evanescent wave hologram may be made is illustrated in FIG. 17. FIG. 17a shows an illuminating beam 70, from a Helium-Neon (HeNe) laser, passing through a beam splitter 72. Beam 73 is reflected off mirrors 76 and 78 and impinges with surface of a holographic film 80. Beam 74 is reflected off mirror 82 and interferes with beam 73 after passing through a high index prism 83. The hologram formed is shown in diagrammatic detail in FIG. 17b. High index liquid 85 allows total internal reflectron at its interface with the film 80. An evanescent region 87 is defined in emulsion 89. The operation of the edge-lit hologram thereby created is described below, with reference to FIG. 18. An advantage of the edge-lit type shown in FIG. 18 is that the optical path 64 can be conveniently defined for location of the illuminating source 62 and the detector. The evanescent wave technique typically provides a hologram of around half a wavelength thickness so that speed and extent of response due to penetration and effect of analyte is improved.

It will be appreciated that the invention has been described by way of examples only and variation to the embodiments described may be made without departing from the scope of the invention.

We claim:

1. A sensor comprising a holographic element which comprises a holographic support medium and a hologram disposed throughout the holographic support medium, wherein at least one optical characteristic of said holographic element varies as a result of a variation of a physical property occurring throughout the holographic support medium, wherein said variation in said physical property results from a reaction between the support medium and an analyte in liquid form to be detected.

2. The sensor according to claim 1 wherein the holographic support medium comprises a biochemical compound and said reaction is a biochemical reaction.

3. The sensor according to claim 2 wherein the compound is disposed throughout the volume of the holographic support medium.

4. The sensor according to claim 1, wherein the physical property which varies is a property selected from the group consisting of:

size of the holographic support medium, shape of the holographic support medium, density of the holographic support medium, viscosity of the holographic support medium, strength of the holographic support medium, hardness of the holographic support medium, polarisability of components of the holographic support medium, charge distribution within the holographic support medium, hydrophobicity of the holographic support medium, solvent swellability of the holographic support medium and integrity of the holographic support medium.

5. The sensor according to claim 1, wherein the optical characteristic which is varied is selected from the group consisting of:

reflectance, refractance and absorbence of the holographic element.

6. The sensor according to claim 1, wherein said sensor comprises at least two holograms.

7. The sensor according to claim 6 wherein the holograms are selected from the group consisting of: transmission holograms, reflection holograms and edge-lit holograms.

8. The sensor according to claim 7 wherein at least one of the reflection, transmission or edge-lit holograms is fabricated so that it is an evanescent hologram.

9. The sensor according to claim 7 wherein at least one of the reflection or transmission holograms is fabricated so that it is a volume hologram.

10. The sensor according to claim 1, wherein the physical property which varies is the depth of modulation of the refractive index disposed throughout the support medium.

11. The sensor according to claim 1, wherein the physical property which varies is the integrity of the support medium.

12. The sensor according to claim 1, wherein the physical property which varies is the size of the support medium.

13. The sensor according to claim 1, wherein a variation in grain size within the holographic element causes a variation in the said, at least one, optical characteristic.

14. The sensor according to claim 1, wherein said species to be detected is an enzyme.

15. The sensor according to claim 1 wherein said species to be detected is labeled with an enzyme.

16. The sensor according to claim 1, wherein said sensor comprises two or more holographic elements arranged so that one of the elements acts as an optical reference for the other of said elements.

17. The sensor according to claim 1, wherein the variation in optical characteristic is detected as an intensity change.

18. The sensor according to claim 1, wherein the variation in optical characteristic is detected as a colour change.

19. The sensor according to claim 1, wherein the variation in optical characteristic is detected as a change in the location of non-ionising radiation emitted by the sensor.

20. The sensor according to claim 1, wherein the variation in optical characteristic is detected as a change in the angle of light emitted by the sensor.

21. A method of operating the sensor according to claim 1, comprising illuminating said sensor while the holographic element is immersed in a liquid.

22. A method of operating the sensor according to claim 1, comprising illuminating said sensor after the liquid analyte has entered the medium while the holographic element is dry.

23. The sensor according to claim 1, wherein the holographic support medium is comprised of gelatin.

* * * * *